United States Patent
Baylin et al.

(10) Patent No.: US 7,371,527 B1
(45) Date of Patent: May 13, 2008

(54) HYPERMETHYLATION OF GATA-4 AND GATA-5 TRANSCRIPTION FACTOR GENES IN CANCER

(75) Inventors: Stephen B. Baylin, Baltimore, MD (US); Yoshimitsu Akiyama, Chiba (JP); James G. Herman, Lutherville, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 170 days.

(21) Appl. No.: 10/972,066

(22) Filed: Oct. 21, 2004

Related U.S. Application Data

(60) Provisional application No. 60/513,271, filed on Oct. 21, 2003.

(51) Int. Cl.
*C12Q 1/68* (2006.01)
(52) U.S. Cl. .......................................... 435/6
(58) Field of Classification Search ................. 435/6
See application file for complete search history.

(56) References Cited

OTHER PUBLICATIONS

Guo et al (Clinical Cancer Research, Dec. 1, 2004, 10: 7917-7924).*
Akiyama et al (Molecular and Cellular Biology, Dec. 2003, p. 8429-8439).*
Tockman et al (Cancer Res., 1992, 52:2711s-2718s).*
Schmitt et al (Molecular Endocrinology, 2002, 16(2): 213-220).*
Brock et al (Proceedings of the American Association for Cancer Research Annual Meeting, Jul. 2003, 44: 493).*
Guo et al (Proceedings of the American Association for Cancer Research Annual Meeting, Jul. 2003, 44:429-430).*
Wiencke et al (Cancer Epidemiology, Biomarkers, and Prevention, Jun. 1999, 8:501-506).*
Clark et al (Nucleic Acids Research, 1994, 22(15):2990-2997).*
Saluz et al (PNAS, 1989, 86:2602-2606).*
Al-azzeh et al., "Transcription Factor GATA-6 Activates Expression of Gastroprotective Trefoil Genes TFF1 and TFF2," *Biochim. Biophys. Acta.*, 1490:324-32 (2000).
Bai et al., "Distinct Expression of CDX2 and GATA4/5, Development-related Genes, in Human Gastric Cancer Cell Lines," *Mol. Carcinog.*, 28:184-8 (2000).
Bird, A., "DNA Methylation Patterns and Epigenetic Memory," *Genes Dev.*, 16:6-21 (2002).
Cameron et al., "Synergy of Demethylation and Histone Deacetylase Inhibition in the Re-expression of Genes Silenced in Cancer," *Nat. Genet.*, 21:103-7 (1999).
Esteller et al., "A Gene Hypermethylation Profile of Human Cancer," *Cancer Res.*, 61:3225-9 (2001).

Fujimoto et al., "DNA Hypermethylation at the pS2 Promoter Region is Associated with Early Stage of Stomach Carcinogenesis," *Cancer Lett.* 149:125-34 (2000).
Fujiwara et al., "Evidence for the Presence of Two Tumor Suppressor Genes on Chromosome 8p for Colorectal Carcinoma," *Cancer Res.*, 53:1172-4 (1993).
Jones et al., "Frequent Loss of Heterozygosity on Chromosome Arm 18q in Squamous Cell Carcinomas. Identification of 2 Regions of Loss—18q11.1-q12.3 and 18q21.1-q23," *Arch. Otolaryngol. Head Neck Surg.*, 123:610-4 (1997).
Jones and Baylin, "The Fundamental Role of Epigenetic Events in Cancer," *Nat. Rev. Genet.*, 3:415-28 (2002).
Ketola et al., "Expression and Regulation of Transcriptions Factors GATA-4 and GATA-6 in Development Mouse Testis," *Endocrinology*, 140:1470-80 (1999).
Lefebvre et al., "Gastric Mucosa Abnormalities and Tumorigenesis in Mice Lacking the ps2 Trefoil Protein," *Science*, 274:259-62 (1996).
Matzuk et al., "Alpha-inhibin is a Tumour-Suppressor Gene with Gonodal Specificity in Mice," *Nature*, 360:313-9 (1992).
Park et al., "Somatic Mutations of the Trefoil Factor Family 1 Gene in Gastric Cancer," *Gastroenterology*, 119:691-8 (2000).
Rhee et al., "CpG Methylation is Maintained in Human Cancer Cells Lacking DNMT1," *Nature*, 404:1003-7 (2000).
Rhee et al., "DNMT1 and DNMT3b Cooperate to Silence Genes in Human Cancer Cells," *Nature*, 416:552-6 (2002).
Schmitt et al., "Hypermethylation of the Inhibin Alpha-Subunit Gene in Prostate Carcinoma," *Mol. Endocrinol.*, 16:213-20 (2002).
Singh et al., "Expression of Oestrogen Receptor and Oestrogen-inducible Genes ps2 and ERD5 in Large Bowel Mucosa and Cancer," *J. Pathol.*, 184:153-60 (1998).
Suzuki et al., "A Genomic Screen for Genes Upregulated by Demethylation and Histone Deacetylase Inhibition in Human Colorectal Cancer," *Nat. Genet.*, 31:141-9 (2002).
van Wering et al., "Physical Interaction between GATA-5 and Hepatocyte Nuclear Factor-1alpha Results in Synergistic Activation of the Human Lactase-phlorizin Hydrolase Promoter," *J. Biol. Chem.*, 277:27659-67 (2002).
Widschwendter and Jones, "DNA Methylation and Breast Carcinogenesis," *Oncogene*, 21:5462-82 (2002).
Wright et al., "Rolling in the Clover: Trefoil Factor Family (TFF)-Domain Peptides, Cell Migration and Cancer," *FEBS Lett.*, 408:121-3 (1997).

\* cited by examiner

*Primary Examiner*—Misook Yu
*Assistant Examiner*—Sean Aeder
(74) *Attorney, Agent, or Firm*—DLA Piper US LLP

(57) ABSTRACT

Methods are provided for identifying the presence of cancer cells in a sample by detecting hypermethylation of the promoter region of a GATA-4 transcription factor gene, a GATA-5 transcription factor gene, or both. Methods for ameliorating a cancer by effecting expression of a hypermethylation silenced GATA-4 and/or GATA-5 transcription also are provided.

19 Claims, 5 Drawing Sheets

HYPERMETHYLATION OF GATA-4 AND GATA-5 TRANSCRIPTION FACTOR GENES IN CANCER

CROSS REFERENCE TO RELATED APPLICATION(S)

This application claims the benefit of priority under 35 U.S.C. § 119(e) of U.S. Ser. No. 60/513,271, filed Oct. 21, 2003, the entire content of which is incorporated herein by reference.

GRANT INFORMATION

This invention was made with government support under Grant No. ES011858-12 awarded by the National Institute of Environmental Health Science. The United States government has certain rights in this invention.

BACKGROUND OF THE INVENTION

1. Field of the Invention

The invention relates generally to methods of diagnosing and monitoring the course of a cancer, and more specifically to methods of detecting cancer cells by detecting methylation silencing of GATA-4 and/or GATA-5 gene(s), which encode transcription regulatory proteins, to methods of diagnosing a cancer in a subject by detecting such methylation silencing in a cell sample obtained from the subject, and to methods of treating a subject having a cancer by effecting expression of methylation silenced GATA-4 and/or GATA-5 in cancer cells of the subject.

2. Background Information

Cancers can occur as a result of genetic changes such as mutations of a gene, as well as epigenetic mechanisms, which are not associated with mutation of a DNA sequence. The most commonly observed epigenetic change involves silencing of gene expression due to methylation of the gene sequence, particularly the 5' upstream gene regulatory sequences. Methylation of cytosine residues located 5' to guanosine in CpG dinucleotides, particularly in CpG-rich regions (CpG islands), often is involved in the normal regulation of gene expression in higher eukaryotes. For example, extensive methylation of CpG islands is associated with transcriptional inactivation of selected imprinted genes, as well as the genes on the inactivated X chromosome in females. Aberrant methylation of normally unmethylated CpG islands also is present in immortalized and transformed cells, and has been associated with transcriptional inactivation of tumor suppressor genes in human cancers.

Changes to genes that are associated with cancer, including mutations that result in loss of expression of gene or in expression of a defective gene product, and epigenetic mechanisms such as methylation-silencing of gene transcription, provide markers useful for determining whether a cell is susceptible to loss of normal growth control and, therefore, potentially a cancer cell. For example, a mutation of the BRCA1 gene has been associated with breast cancer. As such, diagnostic tests can be performed using cells, for example, from a woman with a family history of breast cancer to determine whether the woman has the BRCA1 mutation that is a marker for breast cancer. The prostate specific antigen (PSA) is another example of a marker, in this case for prostate cancer. Although neither the defect resulting in expression of the PSA nor the normal function of PSA in the body is known, PSA nevertheless provides a valuable cancer marker because it allows the identification of men predisposed to prostate cancer or at a very early stage of the disease such that effective therapy can be implemented. More recently, methylation-silenced transcription of a suppressor of cytokine signaling/cytokine-inducible SH2 protein family member, the SOCS-1 gene was found to be associated with various cancers, including hepatocellular carcinoma, multiple myeloma, and acute leukemias. As such, screening assays directed to detecting the methylation status of the SOCS-1 gene can provide diagnostic information relating to such cancers.

Cancer often is a silent disease that does not present clinical signs or symptoms until the disease is well advanced. As such, the availability and use of markers that allow the identification of individuals susceptible to a cancer, or that allow detection of a cancer at an early stage, can be of great benefit. Unfortunately, such markers are not available for most cancers and, as a result, many cancer patients do not seek medical assistance until the cancer is at a stage that requires radical therapy, or is untreatable. Thus, a need exists for markers that can be used to detect cancer cells. The present invention satisfies this need and provides additional advantages.

SUMMARY OF THE INVENTION

The present invention is based, in part, on the discovery that epigenetic (methylation) silencing the genes encoding the transcriptional regulatory proteins GATA-4 and/or GATA-5 occurs in various cancers, including cancers of the gastrointestinal tract, and that downstream genes regulated by GATA-4 and/or GATA-5 also are hypermethylated (methylation silenced). The invention also is based, in part, on the discovery that expression of the epigenetically silenced genes in the cancer cells can be induced using demethylating agents, and, remarkably, that expression of an exogenous GATA-5 in such cells overrides the epigenetic silencing of hypermethylated downstream GATA-5 target genes.

The present invention relates to a method for identifying a cell that exhibits or is predisposed to exhibiting unregulated growth. Such a method can be performed, for example, by detecting, in a test cell, epigenetic silencing of a GATA-4 and/or GATA-5 gene, or of a downstream GATA-4 and/or GATA-5 target gene such as a trefoil (TFF) gene, a Disabled-2 (Dab2) gene, an inhibin α gene, or a combination thereof, thereby identifying the test cell as a cell that exhibits or is predisposed to exhibiting unregulated growth. The cell exhibiting, or predisposed to exhibiting unregulated growth, can be a neoplastic cell, which can be, for example, a premalignant cell such as a cell of a gastrointestinal polyp, or can be a cancer cell, for example, a carcinoma cell such as a colorectal cancer (CRC) cell or a gastric cancer (GC) cell.

In one embodiment, the epigenetic silencing is methylation silencing, and the method for identifying a cell that exhibits or is predisposed to exhibiting unregulated growth is performed by detecting methylation silencing. Methylation silencing can be detected, for example, by contacting a region comprising a 5' regulatory region of the nucleic acid molecule comprising the gene (e.g., GATA-4 and/or GATA-5) with a methylation sensitive restriction endonuclease, which cleaves a recognition site in the 5' regulatory region comprising a methylated cytosine residue of a CpG dinucleotide, whereby cleavage of the nucleic acid molecule is indicative of methylation silencing of the gene of the test cell. For example, the methylation sensitive restriction endonuclease can be Acc III, Ban I, BstN I, Msp I, or Xma I. Alternatively, or in addition, methylation silencing can be detected by contacting a region comprising a 5' regulatory region of the nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. For example, the methylation sensitive restriction endonuclease can be Acc II, Ava I, BssH II, BstU I, Hpa II, or Not I.

Methylation silencing of a gene also can be detected by contacting a 5' regulatory region of the nucleic acid molecule comprising the gene of the test cell with a chemical reagent that selectively modifies either an unmethylated cytosine residue or a methylated cytosine residue, and detecting a product generated due to said contacting, wherein the product is indicative of methylation of a cytosine residue in a CpG dinucleotide of the gene. The product can be detected, for example, using an electrophoresis method, a chromatography method, a mass spectrometry method, or a combination of such methods.

In one aspect of the present method, the chemical reagent is hydrazine, thereby producing a hydrazine treated 5' regulatory region of the gene. Such a method can further include contacting the hydrazine treated 5' regulatory region with a reagent that cleaves hydrazine modified cytosine residues to generate a product comprising fragments of the nucleic acid molecule comprising the gene; separating the fragments according to molecular weight; and detecting a gap at a position known to contain a cytosine residue in the 5' regulatory region of the gene, wherein the gap is indicative of methylation of a cytosine residue in the CpG dinucleotide in the gene. The reagent that cleaves the hydrazine modified cytosine residue can be, for example, piperidine.

In another aspect of the present method, the chemical reagent comprises bisulfite ions, whereby unmethylated cytosine residues in the 5' regulatory region of the gene are converted to bisulfite modified cytosine residues. Such a method can further include exposing the bisulfite ion treated gene to alkaline conditions, whereby bisulfite modified cytosine residues are converted to uracil residues; and detecting an amount or distribution of uracil residues in the 5' regulatory region of the bisulfite ion treated gene of the test cell, wherein a decrease in the amount or distribution of uracil residues in the 5' regulatory region of gene from the test cell, as compared to the amount or distribution of uracil residues in a corresponding bisulfite ion treated unmethylated gene following exposure to alkaline conditions, is indicative of methylation of cytosine residues in CpG dinucleotides in the 5' regulatory region of the gene. The amount or distribution of uracil residues can be detected, for example, by determining the nucleotide sequence of the bisulfite modified 5' regulatory region of the gene following exposure to alkaline conditions. The amount or distribution of uracil residues also can be detected by contacting the bisulfite ion treated gene sequence, following exposure to alkaline conditions, with an oligonucleotide that selectively hybridizes to the 5' region regulatory of the gene containing uracil residues, and detecting selective hybridization of the oligonucleotide.

An oligonucleotide useful in such a method can be any oligonucleotide that selectively hybridizes to the 5' region regulatory of the gene, which can be a GATA gene (e.g., GATA-4 or GATA-5) or a downstream target gene regulated by a GATA transcription regulatory factor (e.g., TFF1, TFF2, TFF3, inhibin α, or Dab2), containing uracil residues.

Examples of such oligonucleotides are shown in Tables 2 to 4 (see Example 1). To facilitate detection, in one aspect the oligonucleotide can include a detectable label, thus providing a means to detect selective hybridization by detecting the label. The detectable label can be any label that is conveniently detectable, including, for example, a radioisotope, a paramagnetic isotope, a luminescent compound, a chemiluminescent compound, a fluorescent compound, a metal chelate, an enzyme, a substrate for an enzyme, a receptor, or a ligand for a receptor. In another aspect, the oligonucleotide can be a substrate for a primer extension reaction, wherein detecting selective hybridization comprises detecting a product of the primer extension reaction. For example, the oligonucleotide (primer) can be a methylation specific primer, which can selectively hybridize to and allow extension of nucleotide sequence comprising a methylated region of the target gene (e.g., GATA-4, GATA-5, TFF1, or Dab2).

An amount or distribution of uracil residues also can be detected, for example, by contacting the 5' regulatory region of a gene with an amplification primer pair comprising a forward primer and a reverse primer under conditions suitable for amplification, wherein at least one primer of the primer pair comprises an oligonucleotide that selectively hybridizes to a nucleotide sequence of the 5' regulatory region containing uracil residues, whereby generation of an amplification product is indicative of methylation of cytosine residues in CpG dinucleotides in the 5' regulatory region of the gene. Amplification primer pairs useful for such a method are exemplified by SEQ ID NOS:38 and 39, 42 and 43, and 50 and 51 (see Table 3, methylation specific primer pairs).

The amount or distribution of uracil residues also can be detected by contacting the 5' regulatory region of the gene with an amplification primer pair comprising a forward primer and a reverse primer under conditions suitable for amplification, wherein both primers of the primer pair selectively hybridize to a nucleotide sequence of the 5' regulatory region containing cytosine residues, but not to a corresponding nucleotide sequence of the 5' regulatory region containing uracil residues, and whereby generation of an amplification product is indicative of a lack of methylation of cytosine residues in CpG dinucleotides in the 5' regulatory region of the gene, thereby detecting methylation silencing of the gene of the test cell. Amplification primer pairs useful for such a method are exemplified by SEQ ID NOS:36 and 37, 40 and 41, and 52 and 53 (see Table 3, unmethylation specific primer pairs).

The amount or distribution of uracil residues also can be detected by contacting the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene.

Methylation silencing of a gene associated with a cancer also can be identified by contacting a test cell with a demethylating agent, and detecting increased expression of an RNA encoded by the gene as compared to a level of expression of the RNA in a test cell not contacted with a demethylating agent. Such a method can further include detecting methylation, if any, of cytosine residues in a CpG dinucleotide in a CpG island of the 5' regulatory region of the gene in a corresponding cell exhibiting regulated growth, or an extract of the corresponding cell The demethylating agent can be a methyltransferase inhibitor such as 5-aza-2'-deoxycytidine (DAC). Increased expression of an RNA can be detected using any method for detecting RNA, including, for example, northern blot analysis, a reverse transcription-polymerase chain reaction (RT-PCR) assay, or selective hybridization to a nucleotide sequence, which can be one of an array of nucleotide sequences. Accordingly, the methods of the invention can be performed in a high throughput format, wherein the test cell, or extract of the test cell, comprises one of a plurality of test cells, or extracts of the test cells, or a combination thereof; and each of the test cells, or extracts of the test cells, of the plurality is the same or different, or a combination thereof. According to a high throughput method of practicing the present invention, the test cells, or extracts of the test cell, can be arranged in an array, which can be an addressable array, on a solid support such as a microchip, a glass slide, or a bead.

A test cell examined according to a method of the invention can be a cell from a cell culture, e.g., an established cell line, or primary cells placed in culture, or can comprise a sample obtained from a subject, for example, a human subject. As such, the sample can be an organ sample, a tissue sample, or a cell sample, for example, an alimentary/gastrointestinal tract tissue sample, a liver sample, a skin sample, a lymph node sample, a kidney sample, a lung sample, a muscle sample, a bone sample, or a brain sample. For example, a gastrointestinal tract sample can include a stomach sample, a small intestine sample, a colon sample, a rectal sample, or a combination thereof. A sample also can comprise a biological fluid sample, for example, a bone marrow, blood, serum, lymph, cerebrospinal fluid, saliva, sputum, stool, urine, or ejaculate sample, which can contain cells therein or products of cells, particularly nucleic acid molecules.

The present invention also relates to a method of reducing or inhibiting unregulated growth of a cell exhibiting epigenetic silenced transcription of at least one gene associated with a cancer. Such a method can be practiced, for example, by restoring expression of a polypeptide encoded by the epigenetic silenced gene in the cell, thereby reducing or inhibiting unregulated growth of the cell. Such expression can be restored, for example, by contacting the cell with a demethylating agent (e.g., a methyltransferase inhibitor), a histone deacetylase inhibitor, or a combination thereof. In one aspect, expression in a cell of epigenetically silenced genes that are regulated by a GATA-5 gene is restored by expressing GATA-5 in the cell, wherein the GATA-5 overrides methylation silencing of the GATA-5 downstream target genes such as a TFF gene, inhibin α gene and/or Dab2 gene.

In one embodiment, expression of a methylation silenced gene in a cell is performed by contacting the cell with at least one demethylating agent, for example, DAC. In one aspect, the cell can be contacted with the demethylating agent in vitro, e.g., in a culture medium or other medium conducive to survival of the cell. If desired, the cell contacted with the demethylating agent further can be administered to a subject, particularly to a subject from which the cell was obtained or to a subject haplotype matched to the subject from which the cell was obtained. In another aspect, the agent can be administered to subject such that the cell exhibiting unregulated growth is contacted with the agent.

In another embodiment, the method includes introducing a polynucleotide encoding a polypeptide, for example, the polypeptide encoded by a methylation silenced gene, into the cell, whereby the polypeptide is expressed from the polynucleotide, thereby restoring expression in the cell of the polypeptide and/or one or more other polypeptides encoded by methylation silenced genes regulated by the polypeptide. For example, where the polynucleotide encodes a GATA protein such as GATA-5, expression of the GATA-5 in the cell can override methylation silencing of downstream GATA-5 target genes (e.g., TFF1 or Dab2), thereby restoring expression of GATA-5, TFF1 and Dab2 in the cell. The polynucleotide can, but need not, be contained in a vector, e.g., a viral vector, and/or can be formulated in a matrix that facilitates introduction of the polynucleotide into a cell, e.g., liposomes or microbubbles. The polynucleotide can be introduced into a cell by contacting the cell with the polynucleotide ex vivo, in which case the cell containing the polynucleotide can, but need not, be administered to a subject. The polynucleotide also can be introduced into a cell by contacting the cell with the polynucleotide in vivo.

The epigenetic silenced gene can be any gene identified using a method as disclosed herein, and examining a particular cell type such as a particular cancer cell type. Epigenetic silenced genes in CRC and/or GC cells are exemplified herein by GATA-4 (see, e.g., GenBank™ Acc. No. NM_002052 (SEQ ID NO:1); GeneID 14463; human chromosome locus ("hcl") 14C3; see, also, GenBank™ Acc. Nos. AC90790 and AC069185); GATA-5 (see, e.g., GenBank™ Acc. No. NM_080473 (SEQ ID NO:2); GeneID 140628; hcl 20q13.33; see, also, GenBank™ Acc. No. AL499627); TFF1 (see, e.g., GenBank™ Acc. No. NM_003225 (SEQ ID NO:3); GeneID 7031; hcl 21q22.3; see, also, GenBank™ Acc. No. AP001746); TFF2 (see, e.g., GenBank™ Acc. No. NM_005423 (SEQ ID NO:4); GeneID 7031; hcl 21q22.3; see, also, GenBank™ Acc. No. AP001746); TFF3 (GenBank™ Acc. No. NM_003226 (SEQ ID NO:5); GeneID 7033; hcl 21q22.3; see, also, GenBank™ Acc. No. AP001746); Dab2 (GenBank™ Acc. No. NM_001343 (SEQ ID NO:6); GeneID 11601; hcl 5p13) and inhibin α (GenBank™ Acc. No. NM_002191 (SEQ ID NO:7); GeneID 3623; hcl 2q33-q36; see, also GenBank™ Acc. Nos. AF272341 and AF218839). For comparison, GATA-6 (see, e.g., GenBank™ Acc. No. NM_205420 (SEQ ID NO:8); GeneID 2627; hcl 18q11.1-q11.2; see, also, GenBank™ Acc. Nos. AC009669), which is not subject to methylation silencing, can be examined. Each of the sequences in the above-cited GenBank™ Acc. Nos. is incorporated herein by reference. Polynucleotide sequences encompassing portions of these genes can be obtained, for example, by PCR of nucleic acid molecules obtained from colorectal cancer cells using amplification primer pairs as disclosed herein or prepared using routine and well known methods based on the disclosed sequences.

The present invention further relates to a method for treating a cancer patient, wherein cancer cells in the patient exhibit epigenetic silenced expression of at least one of a GATA-4 gene, GATA-5 gene, TFF1 gene, TFF2 gene, TFF3 gene, Dab2 gene, and inhibin α gene. Such a method can be performed, for example, by restoring expression of one or more of the epigenetic silenced genes in cancer cells in the patient. For example, where at least one epigenetic silenced gene is a methylation silenced gene, the patient can be treated by administering a demethylating agent to the subject in an amount sufficient to restore expression of the methylation silenced gene(s) in cancer cells in the subject. Alternatively, or in addition, the patient can be treated by administering at least one polynucleotide encoding at least one polypeptide encoded by one or more of the epigenetic silenced genes to the subject under conditions sufficient for expression of the at least one polypeptide in cancer cells in the subject. Where a polynucleotide is administered to the patient, the polynucleotide can be contained in a vector (e.g., a viral vector) preferably an expression vector, and/or can be formulated in a matrix that facilitates uptake of the polynucleotide by a target cancer cell (e.g., in a liposome).

The cancer to be treated according to a method of the invention can be any type of cancer, including, for example, a carcinoma (e.g., CRC and/or GC) or a sarcoma. For example, where the cancer is a CRC and/or a GC, the patient can be treated by restoring expression of one or more epigenetic silenced genes, including GATA-4, GATA-5, TFF1, TFF2, TFF3, Dab2, and inhibin α. As disclosed herein, a patient having a cancer in which, for example, GATA-5 and downstream target genes regulated by GATA-5 such as TFF1 and inhibin α are methylation silenced, can be treated by restoring GATA-5 expression in the cancer cells, wherein GATA-5 can override the methylation silencing of TFF1 and inhibin α, thereby restoring their expression as well (see Example 1).

The present invention also relates to a method for selecting a therapeutic strategy for treating a cancer patient. Such a method can be performed, for example, by identifying at least one methylation silenced gene associated with the cancer, including at least one of GATA-4, GATA-S, TFF1, TFF2, TFF3, Dab2, and inhibin α, according to a method as disclosed herein, and selecting an agent useful for restoring expression of one or more of the identified methylation silenced gene in cancer cells of the patient. For example, the selected agent can be a polynucleotide encoding an identified methylation silenced gene, for example, a polynucleotide encoding GATA-4, GATA-5, TFF1, TFF2, TFF3, Dab2, or inhibin α, or a combination thereof. The selected agent for restoring expression of a methylation silenced gene also can be a demethylating agent such as DAC.

Accordingly, the present invention further relates to a method of treating a subject suffering from a colorectal cancer, a gastric cancer, or both, wherein cells associated with the cancer contain at least one methylation silenced GATA-4, GATA-5, TFF1, TFF2, TFF3, Dab2, or inhibin α gene, or a combination thereof. Such a method can be performed, for example, by administering an amount of an agent that restores expression of the at least one methylation silenced gene to the subject sufficient to restore expression of the methylation silenced gene in cells associated with the cancer. The agent can be a polynucleotide encoding the methylation silenced gene, for example, a polynucleotide encoding GATA-4, GATA-5, TFF1, TFF2, TFF3, Dab2, or inhibin α, or a combination thereof; or can be a demethylating agent such as DAC. An agent useful for treating a subject suffering from a colorectal cancer, a gastric cancer, or both, can be contacted with cells of the cancer ex vivo, after which the cells can be administered back into the patient; or the agent can be administer to a site of the cancer cells in the patient.

The present invention further relates to an isolated oligonucleotide, which has a nucleotide sequence as set forth in SEQ ID NOS:10 to 71, as well as to a plurality of isolated oligonucleotides, which includes at least two of the isolated oligonucleotides as set forth in SEQ ID NOS:10 to 71. In addition, the invention relates to an amplification primer pair, which includes a forward primer and a reverse primer as set forth in SEQ ID NOS:10 and 11, 12 and 13, 14 and 15, etc. through 70 and 71 (see Tables 2 to 4), including, for example, an amplification primer pair can amplify a nucleotide sequence of a GATA-4 (e.g., SEQ ID NOS:16 and 17), GATA-5 (e.g., SEQ ID NOS:18 and 19), TFF1 (e.g., SEQ ID NOS:28 and 29), TFF2 (e.g., SEQ ID NOS:30 and 31), TFF3, (e.g., SEQ ID NOS:32 and 33), Dab2 (e.g., SEQ ID NOS:22 and 23, or 24 and 25), or inhibin α gene (e.g., SEQ ID NOS:26 and 27). In one aspect, an amplification primer pair of the invention can be used to specifically amplify a methylated 5' regulatory region of the nucleic acid molecule, such amplification primer pairs being exemplified by SEQ ID NOS:41 and 42, which can amplify GATA-5 having a methylated 5' regulatory region. In another aspect, an amplification primer pair of the invention can be used to specifically amplify an unmethylated 5' regulatory region of the nucleic acid molecule, such amplification primer pairs being exemplified by SEQ ID NOS:40 and 41, which can amplify an unmethylated 5' regulatory region of GATA-5 (see Table 3).

The present invention also relates to a kit, which contains at least one isolated oligonucleotide of the invention, including, for example, a plurality of such isolated oligonucleotides (e.g., one or more of SEQ ID NOS:10 to 71). In one embodiment, a plurality of isolated oligonucleotides of a kit of the invention includes at least one amplification primer pair (i.e., a forward primer and a reverse primer), and can include a plurality of amplification primer pairs, including, for example, amplification primer pairs useful for amplifying a methylated or unmethylated GATA-4, GATA-5, TFF1, TFF2, TFF3, Dab2, or inhibin α gene (see Table 3), or combinations thereof. As such, a kit of the invention can contain, for example, one or a plurality of methylation specific amplification primer pairs, unmethylation specific amplification primer pairs, or a combination of methylation specific amplification primer pairs and unmethylation specific amplification primer pair, including methylation specific primer pairs and unmethylation specific primer pairs useful for amplifying a methylated form or an unmethylated form of a particular gene that is known to be or suspected of being methylation silenced in one or more types of cancer cells.

A kit of the invention can further include additional reagents, which can be useful, for example, for a purpose for which the oligonucleotides of the kit are useful. For example, where a kit contains one or a plurality of methylation specific and/or unmethylation specific amplification primers, the kit can further contain, for example, control polynucleotides, which can be methylated or unmethylated; one or more reagents that modify methylated cytosine residues, and/or one or more reagents for performing an amplification reaction. Where the kit contains one or plurality of oligonucleotides that selectively hybridize to a methylated or to an unmethylated gene sequence, the kit can further contain, for example, a methylation sensitive restriction endonuclease.

BRIEF DESCRIPTION OF THE DRAWINGS

FIG. 1A provides a representation of the GATA-4 gene. The diagram includes a new exon 1, located 3.5 kilobases (kB) upstream of the previously designated exon 1, which was identified from the human expressed sequence tag (EST; Acc. No. BG718444), genomic sequences containing this EST (Acc. Nos. AC090790 and AC069185), and a confirmatory PCR approach, in which the EST was contained in the single transcript amplified for this gene.

FIG. 1B provides a representation of the GATA-5 gene. The newly reported GATA-5 cDNA (GenBank™ Acc No. NM_080473; SEQ ID NO:2) includes one 5'-untranslated exon (41 base pairs (bp)). This newly identified exon 1 is located 387 bp upstream of exon 2, which contains the translation start site in the genomic GATA-5 sequence (No. AL499627).

FIG. 1C provides a representation of the GATA-6 gene. The data for the genomic structure of GATA-6 (A and B) was obtained from the newly reported sequence of this gene (GenBank™ Acc. No. AC009669) which reveals two 5'-untranslated exons (1a and 1b).

FIG. 2A provides a summary of the analyses of GATA-4 and GATA-5 methylation in 45 primary colorectal cancers. Each number in the vertical column represents a single tumor. Black=detection of methylated alleles; white=detection of unmethylated alleles only.

FIG. 2B provides an MSP analyses for normal colon mucosa samples from patients without (n=2) and with (n=12) cancer. Grey boxes=weak detection of methylated alleles in two patients with GATA-4 simultaneously hypermethylated in cancer.

FIG. 2C provides a summary of methylation status for 27 primary gastric cancers.

FIG. 4A shows the methylation status of the inhibin α gene. A schematic of the 5' region of the gene is shown in the upper panel, in which the square depicts the first exon and the blackened area denotes the coding region within this exon. The black triangles represent positions of consensus GATA binding sites and the vertical lines each represent a CpG site. The large arrow (BS) denotes a region of bisulfite sequencing for the CpG poor region previously thought to be the only promoter region (see text) and the smaller arrows, (MSP), represent the positions of primers used for the MSP analysis, in all the cancer cell lines, of the newly defined CpG island discussed in the text and shown in the panel below where U=unmethylated alleles and M=methylated alleles. PBL=normal lymphocytes; N.C=normal colon; H₂O=no DNA added.

FIG. 4B shows the methylation status of Dab2. A schematic of the Dab2 gene is shown in the upper panel, in which a 5' untranslated exon 1 (open box) is located upstream from exon 2, which contains the ATG for start of the coding region (black area within the square for exon 2). Arching line=the mRNA splicing which joins exon 1 to exon 2; black triangles=positions of GATA binding sites; vertical lines=CpG sites and the island around exon 1; arrows at the bottom (MSP)=position of MSP primers used to analyze the methylation status of the CpG island as shown in the panel below. Lower panel depicts examples of MSP results for the methylation status of the Dab2 5' CpG island. U=unmethylated alleles; M=methylated alleles; PBL=normal lymphocytes; N.C=normal colon; C1C and C2C=colon cancers.

FIG. 5A provides a schematic of the alignment of the three TFF genes on chromosome 21q22.3. The location of a separate gene, TMPRSS3, upstream from TFF1 is also shown. No CpG islands were identified along the depicted stretch of genomic sequence.

FIG. 5B shows the methylation status of TFF1. A schematic of the 5' region of the gene depicting the transcription start site (large vertical arrow) and exon 1 is shown in the square with the coding region portion shown in black. Vertical black triangles=GATA binding sites; Vertical lines=CpG sites; Horizontal arrows (MSP) show the primer sites for the MSP analysis in the panel below for selected cancer cell lines and normal tissues (N.C=normal colon; PBL=peripheral blood lymphocytes).

FIG. 5C provides a schematic for the 5' region of TFF2. All symbols are as in those in FIG. 5A except that the horizontal arrow (BS) shows the area represented in the bisulfite sequencing shown directly beside the schematic. For the sequencing all horizontal squares represent CpG sites in individual sequenced clones and white=unmethylated, while black=methylated. The sequencing is shown for HT29 cells, in which the gene is expressed, and HCT116 cells, in which it is not and these same cells which express the gene following adenoviral expression of GATA-5.

FIG. 5D provides a schematic for the 5' region of TFF3. All symbols are as in FIG. 5A, except the horizontal arrow (BS) shows the area represented in the bisulfite sequencing shown directly beside the schematic.

DETAILED DESCRIPTION OF THE INVENTION

Figure 1A:
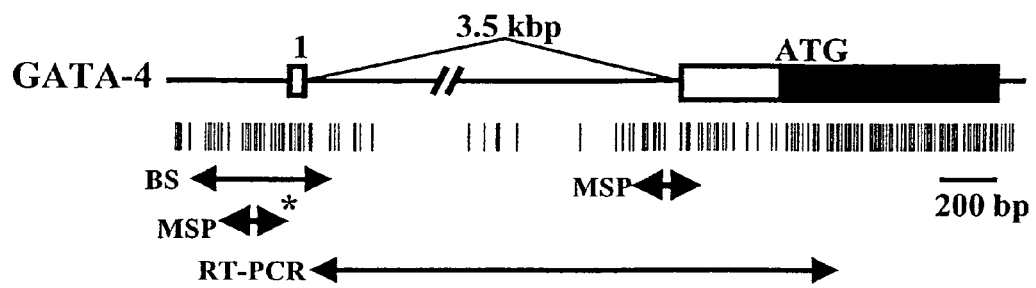
FIGS. 1A to 1C provide schematic representations of 5' regions of GATA-4, GATA-5 and GATA-6, and MSP analyses of promoter methylation status. Boxes indicate exons including coding (black) and non-coding (white) regions. Vertical bars show CpG sites. Black arrows below the CpG sites indicate the regions analyzed by methylation specific PCR (MSP), genomic sequencing (GS) and bisulfite sequencing (BS). The regions analyzed by MSP, for which methylation status corresponded to GATA-4, GATA-5 and GATA-6 expression are indicated by an asterisk (*).

The present invention is based on the discovery that methylation silencing of GATA-4 and GATA-5 genes, which encode GATA-4 and GATA-5 transcription regulatory proteins, respectively, and of downstream target genes, occurs in various cancers, including, for example, gastrointestinal (GI) tract cancers. As such, the present invention provides methods of detecting cancer cells, for example, in a sample obtained from a subject to be examined for cancer; methods of diagnosing cancer in a subject; and methods of monitoring the progression of a cancer and/or effectiveness of a treatment for the cancer. In addition, the invention provides methods of inducing expression of GATA-4 and/or GATA-5 target genes (i.e., genes that are regulated by GATA-4 and/or GATA-5) in cells in which GATA-4 and/or GATA-5 and the target genes are epigenetically silenced. Accordingly, methods of treating a cancer also are provided.

The term "epigenetically silenced" or "epigenetic silenced", when used in reference to a gene, means that the gene is not being transcribed, or is being transcribed at a level that is decreased with respect to the level of transcription of the gene in a corresponding control cell (e.g., a normal cell), due to a mechanism other than a genetic change. Epigenetic mechanisms of gene silencing are well known and include, for example, hypermethylation of CpG dinucleotides in a CpG island of the 5' regulatory region of a gene, and structural changes in chromatin due, for example, to histone acetylation, such that gene transcription is reduced or inhibited. Methods for detecting epigenetic silencing of a gene are disclosed herein and include, for example, detecting re-expression (reactivation) of the gene following contact of a cell with an agent that relieves the epigenetic silencing, for example, with a demethylating agent where the silencing is due to hypermethylation.

As used herein, the term "methylation" or "hypermethylation", when used in reference to a gene, means that cytosine residues of CpG dinucleotides in a CpG island associated with the gene are methylated at the 5'-position, i.e., 5'-methylcytosine. The term "methylation status" is used herein to refer to a relative abundance, including the presence or absence, of methylated cytosine residues of CpG dinucleotides in a CpG island. In general, the cytosine residues in a CpG island are not methylated in a transcriptionally active gene and, therefore, the detection of methylated cytosine residues in a CpG island indicates that expression of the gene is reduced or inhibited. Accordingly, as discussed above, reference herein to a "methylation silenced" gene means that the gene is not being transcribed, or is being transcribed at a level that is decreased with respect to the level of transcription of the gene in a corresponding control cell (generally a normal cell) due to hypermethylation of CpG dinucleotides in a CpG island of the 5' regulatory region of the gene. A consequence of methylation silenced gene expression is that a cell containing the gene has reduced levels of, or completely lacks, a polypeptide encoded by the gene (i.e., the gene product) such that any function normally attributed to the gene product in the cell is reduced or absent.

As disclosed herein, methylation silencing of GATA genes, including GATA-4 and GATA-5, was detected in cancer cells, including CRC cancer cells and GC cancer cells. GATA factors comprise a small family of transcription regulatory proteins that contain two conserved zinc finger DNA binding domains for the consensus sequence (WGATAR; SEQ ID NO:9). A network of genes, many of which encode anti-tumor factors, is modulated by the GATA family to help guide normal development of, and adult differentiation in, the GI tract. As disclosed herein, epigenetically mediated silencing, involving both the upstream GATA and downstream target genes, provides a hierarchy of summated gene silencing events to maximally inactivate an anti-tumor network in GI tumorigenesis. Normally, in GI epithelium, GATA-4 and GATA-5 help drive GI differentiation, while GATA-6 is associated with proliferation (as compared to differentiation) in this setting. Methylation specific PCR (MSP) and reverse transcription PCR (RT-PCR) revealed that cultured and primary CRC and GC cancers frequently, and often simultaneously, harbored promoter hypermethylation and transcriptional silencing of GATA-4 and GATA-5, but not GATA-6.

Anti-tumor target genes of GATA-4 and GATA-5, including the trefoil factors (TFFs), inhibin α, and disabled-2 (Dab2), were also silenced, with associated methylation of the promoters, in GI cancers. Drug (5-aza-2'-deoxycytidine; "DAC") or genetically induced (biallelic knockout of the DNA methyltransferases, DNMT1 and DNM3b) demethylation simultaneously re-expressed the silenced upstream and downstream genes. Over-expression of GATA-5 protein also induced re-expression of TFF1, inhibin α, and Dab2 in GI cancer cells, without eliminating the methylation of the promoters of these genes. These results demonstrate that silencing of the upstream transcription factors occurs during tumorigenesis because their expression can otherwise override silencing of the promoters of their downstream target genes. As such, epigenetic events can cooperate and/or summate in GI cancers to disrupt an entire network of tumor suppressor genes.

GATA factors are a family of transcription regulatory proteins containing two conserved zinc finger DNA binding domains, which, as mentioned above, recognize the sequence WGATAR (SEQ ID NO:1; see Refs. 28, 39; citations follow Example 1). GATA-1, GATA-2, and GATA-3 are involved in development and differentiation of the hematopoietic cell lineage (26). GATA-4, GATA-5, and GATA-6 are involved in the development and differentiation of endoderm-derived organs (24), including, for example, induction of embryonic stem cell differentiation (11), specification of proper gut embryogenesis, and guidance of epithelial cell differentiation in the adult (14, 22, 29, 31). GATA-4, GATA-5, and GATA-6 also have been implicated in cancer development. The GATA-6 gene is expressed predominantly in proliferating progenitor cells (14, 22, 29, 31). In contrast, GATA-4 and GATA-5 have the characteristics of tumor suppressor genes because increased expression levels correlate with terminal differentiation in intestinal epithelium (14) and with terminal differentiation induced by sodium butyrate in colorectal cancer (CRC) cells (14, 20); decreased GATA-6 expression was observed in these cases, and may have a repressive effect on GATA-4 (14). Diminished GATA-4 and/or GATA-5 expression was reported in serous ovarian cancers (23) and in gastric cancer (GC) (3), and the chromosome regions for GATA-4, 8p23.1-p22 (23), and GATA-5, 20q13.2-q13.3 (32), are frequent targets of deletion in cancer (13, 18). GATA proteins bind to the promoters of a number of proposed anti-tumor genes, suggesting they act as transcriptional activators.

Despite growing evidence linking the loss of GATA-4 and GATA-5 and downstream target functions to cancer development, mutations in these genes have not been frequently found. As disclosed herein, a high incidence for epigenetic silencing of GATA-4 and GATA-5 was detected in human CRC and GC. Remarkably, a series of proposed downstream GATA target anti-tumor genes also were silenced, and had associated epigenetic silencing marks at their promoters. Both the upstream and downstream genes were simultaneously reactivated by drug and genetic demethylating strategies. Further, over-expression of GATA-5, alone activated the target genes. These results indicate that a hierarchy of related gene silencing events cooperate to drive the progression of individual tumors. The present results also indicate that GATA-4, GATA-5, inhibin α, Dab2, and the TFF genes encode tumor suppressors, which are not expressed due to epigenetic silencing in cancers, including CRC and GC. In addition to growing evidence that loss of function of GATA-4 and GATA-5 genes has a role in cancer, inhibin α and TFF1 both induced tumors when knocked out in mice (25, 27). The present results further support a tumor suppressor role for TFF2, which was homozygously disrupted in two GI cancer cell lines and epigenetically silenced.

The present invention provides methods of detecting a cancer by identifying methylation silencing of at least one of GATA-4, GATA-5, TFF1, TFF2, TFF3, inhibin α, and Dab2. The cancer can be, for example, a carcinoma or a sarcoma, including one or more specific types of cancer, e.g., an alimentary/gastrointestinal tract cancer, a liver cancer, a skin cancer, a breast cancer, an ovarian cancer, a prostate cancer, a lymphoma, a leukemia, a kidney cancer, a lung cancer, an esophageal cancer, a muscle cancer, a bone cancer, or a brain cancer. As disclosed herein, methylation silenced GATA-4, GATA-5, TFF1, TFF2, TFF3, inhibin α, and/or Dab2 genes were detected in association with CRC and/or GC.

The silencing of gene transcription associated with aberrant DNA methylation of CpG dinucleotides in normally unmethylated gene promoter regions is the most widely studied epigenetic abnormality in tumorigenesis. The binding of protein complexes consisting of methyl-CpG-binding domains, transcriptional co-repressors, chromatin remodeling proteins and histone deacetylases to hypermethylated DNA regions results in a transcriptionally repressed (silenced) chromatin state. In eukaryotic cells, methylation of cytosine residues that are immediately 5' to a guanosine residue occurs predominantly in CG poor regions. In contrast, CpG islands generally remain unmethylated in normal cells, except during X chromosome inactivation and parental specific imprinting, where methylation of 5' regulatory regions is associated with transcriptional repression. De novo methylation of the retinoblastoma (Rb) gene has been demonstrated in a small fraction of retinoblastomas (Sakai et al., *Am. J. Hum. Genet.* 48:880, 1991), and aberrant methylation of the VHL gene was found in a subset of sporadic renal cell carcinomas (Herman et al., *Proc. Natl. Acad. Sci. USA* 91:9700-9704, 1994). Expression of a tumor suppressor gene can also be abolished by de novo DNA methylation of a normally unmethylated 5' CpG island (see, for example, Issa et al., *Nature Genet.* 7:536, 1994; Merlo et al., *Nature Med.* 1:686, 1995; Herman et al., *Cancer Res.* 56:722, 1996).

The present invention provides a method for identifying a cell that exhibits or is predisposed to exhibiting unregulated growth by detecting, in a test cell, epigenetic silencing of at least one GATA-4, GATA-5, TFF1, TFF2, TFF3, inhibin α, or Dab2 gene, or a combination of such genes. The cell exhibiting, or predisposed to exhibiting unregulated growth, can be a neoplastic cell, which can be, for example, a premalignant cell such as a cell of a gastrointestinal polyp, or can be a cancer cell, for example, a carcinoma cell such as a CRC cell or a GC cell, or a sarcoma cell. In one embodiment, a method of the invention is practiced by comparing the methylation status of a gene in a test cell or sample with the methylation status of a corresponding gene in a corresponding cell exhibiting regulated growth. As used herein, the term "corresponding" means a reference material, with which a test material is being compared. Generally, the reference material provides a control or standard with which the test material is compared. For example, reference to a corresponding unmethylated GATA-5 gene, with respect to a GATA gene being examined for methylation status, means that the unmethylated GATA gene is the same type of gene as the GATA gene being examined for methylation status, e.g., the test gene and the corresponding unmethylated gene are both a human GATA-5 gene. Reference to a corresponding cell exhibiting regulated growth, with respect to a test cell, generally refers to a normal cell, i.e., a cell that has a cell cycle and growth pattern characteristic of a population of such cells in a healthy individual, for example, a normal colon epithelial cell where the test cell being examined is suspected of being a CRC cell.

A method of the invention is practiced using a sample comprising a test cell, or an extract of the test cell that includes nucleic acid molecules of the cell, particularly genomic DNA, including all or a portion comprising the CpG island of a 5' regulatory region of the gene that is to be examined for methylation status. Generally, the test cell is a cell that is suspected of being a cell that exhibits unregulated growth, for example, a biopsy sample of suspicious lesion, or is a cell that is (or was) in proximity to a premalignant or malignant cell, for example, cell samples taken at one or few places outside of the region of a suspicious lesion, such test cell providing an indication, for example, of the extent to which a surgical procedure should be performed, or a cell sample taken from a surgical margin, such test cells being useful for determining whether a cancer has been completely removed, or for determining whether a cancer has recurred.

A test cell examined according to a method of the invention can be a primary cell that has been obtained from a subject and placed in culture, for example, for the purpose of establishing a primary cell culture that exhibits substantially the same growth characteristics as the cells from which the culture was established, or for the purpose of treating and/or expanding the cells for readministration to the subject. For example, colon epithelial cells can be obtained from a cancer patient suffering from a CRC, wherein the cells exhibit methylation silenced expression of one or more genes associated with the cancer. The cells can be treated in culture using one or more agent to be tested for an ability to restores expression of the silenced gene(s), thus providing a means to identify an agent that can be useful for treating the cancer patient, or another patient having a CRC characterized by methylation silencing of one or more of the same genes.

A test cell can be obtained from a subject in any way typically used in clinical setting for obtaining a sample containing the cells. For example, the test cells (or a sample comprising the test cells) can be obtained by a biopsy procedure such as a needle biopsy of an organ or tissue containing the cells to be tested. As such, the test cells can be obtained from a gastrointestinal tract sample (e.g., a biopsy of a polyp), a liver sample, a bone marrow sample, a skin sample, a lymph node sample, a kidney sample, a lung sample, a muscle sample, a bone sample, a brain sample, or the like. The test cell also can be a component of a biological fluid, for example, blood, lymph, cerebrospinal fluid, saliva, sputum, stool, urine, or ejaculate. If appropriate, the test cells also can be obtained by lavage, for example, for obtaining test cells from the colon, uterus, abdominal cavity, or the like, or using an aspiration procedure, for example, for obtaining a bone marrow sample.

A method of the invention also can be practiced using an extract of a test cell, wherein the extract includes nucleic acid molecules of the test cell, particularly genomic DNA, including all or a CpG island containing portion of the gene or genes to be examined, or RNA where restoration of expression is to be examined. The extract can be a crude extract comprising, for example, a freeze-thawed sample of a tissue containing the test cells; can comprise partially purified genomic DNA, which can include, for example, components of the nuclear matrix; or can comprise substantially purified genomic DNA, which is obtained, for example, following treatment with a protease and alcohol precipitation. In certain embodiments, the test cell also can be a component of a histologic sample that is embedded in paraffin.

Where the epigenetic silencing includes methylation silencing, the method for identifying a cell that exhibits or is predisposed to exhibiting unregulated growth can be performed by detecting methylation of one or more target genes (e.g., GATA-4, GATA-5, TFF1, TFF2, TFF3, inhibin α, and/or Dab2) in the cell. Methylation of a CpG dinucleotide in a CpG island of a gene can be detected using any of various well known methods for detecting CpG methylation of a nucleic acid molecule. Such methods include contacting the gene with one or a series of chemical reagents that selectively modify either unmethylated cytosine residues or methylated cytosine residues, but not both, such that the presence or absence of the modification can be detected; contacting the gene sequence with a methylation sensitive restriction endonuclease, which has a recognition site that includes a CpG dinucleotide, and that cleaves a recognition site either having a methylated cytosine residue of the CpG or lacking a methylated cytosine residue of the CpG, but not both, such that the presence or absence of cleavage of the sequence can be detected; or contacting a nucleic acid molecule comprising the gene with an oligonucleotide probe, primer, or amplification primer pair that selectively hybridizes to the gene sequence and allows a determination to made as to whether the CpG methylation is present. Examples of such methods are provided herein, and modifications and variations on such methods are well known in the art.

Methylation of a target gene (e.g., GATA-4 and/or GATA-5) can be detected, for example, by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, whereby cleavage of the nucleic acid molecule is indicative of methylation and, therefore, methylation silencing of the gene of the test cell. Methylation sensitive restriction endonucleases are well known and include, for example, Acc III, Ban I, BstN I, Msp I, and Xma I. Alternatively, or in addition, methylation silencing can be detected by contacting a region comprising a 5' regulatory region of a nucleic acid molecule comprising the gene with a methylation sensitive restriction endonuclease, which cleaves a recognition site in the 5' regulatory region comprising a methylated cytosine residue of a CpG dinucleotide, provided the cytosine residue of the CpG dinucleotide is unmethylated, whereby a lack of cleavage of the nucleic acid molecule is indicative of methylation silencing of the gene of the test cell. Such methylation sensitive restriction endonucleases are exemplified by Acc II, Ava I, BssH II, BstU I, Hpa II, and Not I.

The presence or absence of cleavage of a nucleic acid molecule comprising a target gene sequence by a methylation sensitive restriction endonuclease can be identified using any method useful for detecting the length or continuity of a polynucleotide sequence. For example, cleavage of the target gene sequence can be detected by Southern blot analysis, which allows mapping of the cleavage site, or using any other electrophoretic method or chromatographic method that separates nucleic acid molecules on the basis of relative size, charge, or a combination thereof. Cleavage of a target gene also can be detected using an oligonucleotide ligation assay, wherein, following contact with the restriction endonuclease, a first oligonucleotide that selectively hybridizes upstream of and adjacent to a restriction endonuclease cleavage site and a second oligonucleotide that selectively hybridizes downstream of and adjacent to the cleavage site are contacted with the target gene sequence, and further contacted with a ligase such that, in the absence of cleavage the oligonucleotides are adjacent to each other and can be ligated together, whereas, in the absence of cleavage, ligation does not occur. By determining the size or other relevant parameter of the oligonucleotides following the ligation reaction, ligated oligonucleotides can be distinguished from unligated oligonucleotides, thereby providing an indication of restriction endonuclease activity.

Methylation silencing of a gene also can be detected by contacting a 5' regulatory region of the nucleic acid molecule comprising the gene of the test cell with a chemical reagent that selectively modifies either an unmethylated cytosine residue or a methylated cytosine residue, and detecting a product generated due to said contacting, wherein the product is indicative of methylation of a cytosine residue in a CpG dinucleotide of the gene, thereby detecting methylation silencing of the gene of the test cell. For example, the product can be detected using an electrophoresis method, a chromatography method, a mass spectrometry method, or a combination of such methods.

In one aspect of this embodiment, the gene is contacted with hydrazine, which modifies cytosine residues, but not methylated cytosine residues, then the hydrazine treated gene sequence is contacted with a reagent such as piperidine, which cleaves the nucleic acid molecule at hydrazine modified cytosine residues, thereby generating a product comprising fragments. By separating the fragments according to molecular weight, using, for example, an electrophoretic, chromatographic, or mass spectrographic method, and comparing the separation pattern with that of a similarly treated corresponding unmethylated gene sequence, gaps are apparent at positions in the test gene contained methylated cytosine residues. As such, the presence of gaps is indicative of methylation of a cytosine residue in the CpG dinucleotide in the target gene of the test cell.

In another aspect, a nucleic acid molecule comprising the target gene is contacted with a chemical reagent comprising bisulfite ions, for example, sodium bisulfite, which converts unmethylated cytosine residues to bisulfite modified cytosine residues, then the bisulfite ion treated gene sequence is exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. As such, the sulfonate group can be removed by exposure to alkaline conditions, resulting in the formation of uracil. The DNA then can amplified, for example, by PCR, and sequenced to determine the methylation status of all CpG sites.

Uracil is recognized as a thymine by Taq polymerase and, upon PCR, the resultant product contains cytosine only at the position where 5-methylcytosine was present in the starting template DNA. By comparing the amount or distribution of uracil residues in the bisulfite ion treated gene sequence of the test cell with a similarly treated corresponding unmethylated gene sequence, detection of a decrease in the amount or distribution of uracil residues in the gene from the test cell is indicative of methylation of cytosine residues in CpG dinucleotides in the target gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide.

As used herein, the term "selective hybridization" or "selectively hybridize" or "specific hybridization" refers to an interaction of two nucleic acid molecules that occurs and is stable under moderately stringent or highly stringent conditions. As such, selective hybridization preferentially occurs, for example, between an oligonucleotide and a target nucleic acid molecule, and not substantially between the oligonucleotide and a nucleic acid molecule other than the target nucleic acid molecule, including not with nucleic acid molecules encoding related but different members of a gene family (e.g., an oligonucleotide that selectively hybridizes with a GATA-4 gene sequence does not substantially cross-hybridize with a GATA-5 gene sequence). An oligonucleotide useful as a probe or primer that selectively hybridizes to a target nucleic acid molecule is at least about 12 to 15 nucleotides in length, generally at least about 18 to 20 nucleotides in length, usually at least about 21 to 25 nucleotides in length, and particularly about 26 to 35 nucleotides in length or. Examples of oligonucleotides useful in practicing the methods of the invention are disclosed herein as SEQ ID NOS:10 to 71, which include amplification primer pairs useful for RT-PCR (see Table 2), methylation specific and unmethylation specific PCR (see Table 3), and bisulfite sequencing (see Table 4).

Conditions that allow for selective hybridization can be estimated based on the annealing temperatures used for the amplification primer pairs (see Tables 2 to 4), determined empirically, or can be estimated based, for example, on the relative GC:AT (or GC:AU) content of the hybridizing oligonucleotide and the target nucleic acid molecule, the length of the hybridizing oligonucleotide, and the number, if any, of mismatches between the oligonucleotide and target sequence to which it is to hybridize (see, for example, Sambrook et al., "Molecular Cloning: A laboratory manual (Cold Spring Harbor Laboratory Press 1989)). As such, the conditions used to achieve a particular level of stringency will vary, depending on the nature of the hybridizing nucleic acid molecules. An additional consideration is whether one of the nucleic acids is immobilized, for example, on a filter. An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 62° C. (high stringency conditions). Hybridization and/or washing can be carried out using only one of these conditions, for example, high stringency conditions, or each of the conditions can be used, for example, for 10 to 15 minutes each, in the order listed above, repeating any or all of the steps listed.

Selective hybridization of an oligonucleotide with a target gene (e.g., a GATA-5 gene) can be detected, for example, by performing the method using an oligonucleotide that includes a detectable label. The detectable label can be any molecule that conveniently can be linked to the oligonucleotide and detected using readily available equipment. For example, the detectable label can be a fluorescent compound such a Cy3, Cy5, Fam, fluorescein, rhodamine, or a green fluorescent protein or enhanced or modified form thereof; a radionuclide such as sulfur-35, technicium-99, phosphorus-32, tritium or iodine-125; a paramagnetic spin label such as carbon-13, Gd-157, Mn-55, Dy-162, Cr-52, or Fe-56; a luminescent compound such as an aequorin; a chemiluminescent compound; a metal chelate; an enzyme such as luciferase or Θ-galactosidase, or a substrate for an enzyme; or a receptor or a ligand for a receptor, for example, biotin. The means for detecting the detectable label will be selected based on the characteristics of the label, as will the means for linking the label to an oligonucleotide (see, for example, Hermanson, "Bioconjugate Techniques" (Academic Press 1996), which is incorporated herein by reference).

Selective hybridization also can be detected, for example, by utilizing the oligonucleotide as a substrate for a primer extension reaction, further contacting the sample with deoxyribonucleotides (dNTPs), including, if desired, a detectable dNTP (e.g., a fluorescently labeled dNTP, a digoxigenin labeled dNTP, or a biotin labeled dNTP), and a DNA dependent DNA polymerase under conditions sufficient for the primer extension reaction to proceed, and detecting a product of the primer extension reaction. Conditions for performing a primer extension reaction are well known in the art (see, for example, Sambrook et al., supra, 1989).

The amount or distribution of uracil residues in a bisulfite ion treated nucleic acid molecule comprising a target gene sequence following exposure to alkaline conditions also can be detected using an amplification reaction such as PCR. An amplification reaction is performed under conditions that allow selective hybridization of the forward and reverse primers of an amplification primer pair to the target nucleic acid molecule. Generally, the reaction is performed in a buffered aqueous solution, at about pH 7-9, usually about pH 8. In addition, the reaction generally is performed in a molar excess of primers to target nucleic acid molecule, for example, at a ratio of about 100:1 primer:genomic DNA. Where the amount of the target nucleic acid molecule in a sample is not known, for example, in a diagnostic procedure using a biological sample, a range of primer amounts can be used in samples run in parallel, although generally even the addition of a small amount of primers will result in a sufficient molar excess such that the amplification reaction can proceed.

The deoxyribonucleoside triphosphates, dATP, dCTP, dGTP, and dTTP, can be added to the synthesis mixture either separately or as a mixture, which can further include the primers, in adequate amounts and the resulting solution is heated to about 90°-100° C. from about 1 to 10 minutes, generally from 1 to 4 minutes. After this heating period, the solution is allowed to cool to room temperature, which is preferable for the primer hybridization. To the cooled mixture is added an appropriate agent for effecting the primer extension reaction, generally a polymerase, and the reaction is allowed to occur under conditions as disclosed herein (see Example 1) or otherwise known in the art. Where the polymerase is heat stable, it can be added together with the other reagents. The polymerase can be any enzyme useful for directing the synthesis of primer extension products, including, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes, as are well known in the art and commercially available. The amplification products can be identified as methylated or non-methylated by a sequencing method, oligomer restriction (Saiki et al., *BioTechnology* 3:1008-1012, 1985), allele-specific oligonucleotide probe analysis (Conner et al., *Proc. Natl. Acad. Sci. USA* 80:278, 1983), oligonucleotide ligation assays (Landegren et al., *Science* 241:1077, 1988), and the like (see, also, Landegren et al., *Science* 242:229-237, 1988).

In one embodiment, the amplification is performed by contacting the target gene sequence (e.g., GATA-4, GATA-5, TFF1, TFF2, TFF3, inhibin α, and/or Dab2 gene) with an amplification primer pair comprising a forward primer and a reverse primer under conditions suitable for amplification, wherein at least one primer of the primer pair comprises an oligonucleotide that selectively hybridizes to a target gene sequence containing uracil residues, whereby generation of an amplification product is indicative of methylation of cytosine residues in CpG dinucleotides in the target gene of the test cell. In another embodiment, the amplification reaction is performed by contacting the target gene sequence with an amplification primer pair comprising a forward primer and a reverse primer under conditions suitable for amplification, wherein both primers of the primer pair selectively hybridize to a target gene sequence containing cytosine residues, but not to a target gene sequence containing uracil residues, whereby generation of an amplification product is indicative of a lack of methylation of cytosine residues in CpG dinucleotides in the target gene of the test cell. Such amplifications can be performed as individual target gene sequence amplification reactions, or can be performed as multiplex reactions.

In still another embodiment, a methylation-specific amplification reaction such as methylation-specific PCR (MSP) is used alone, or in combination with bisulfite treatment, to detect the methylation status of a nucleic acid molecule (see U.S. Pat. Nos. 6,265,171; 6,200,756; and 6,017,704, each of which is incorporated herein by reference; see, also, Example 1). MSP is a particularly sensitive method that allows detection of low numbers of methylated alleles and the use of small amounts of a nucleic acid sample, including paraffin-embedded materials, and also can be conveniently adapted to a multiplex analysis, including, for example, simultaneous detection of unmethylated and methylated products in a single sample, thus providing an internal control.

The amplification primer pairs used in an MSP reaction are designed to specifically distinguish between bisulfite untreated or unmodified DNA, and methylated and unmethylated DNA. MSP primer pairs for unmethylated DNA (unmethylation specific primer pairs) generally have a thymidine residue in the 3'-CpG pair to distinguish it from the cytosine residue retained in methylated DNA, and the complement is designed for the antisense primer. MSP primer pairs usually contain relatively few cytosine or guanine residues in the sequence because cytosine is absent in the sense (forward) primer and the guanine is absent in the antisense (reverse) primer; cytosine becomes modified to uracil, which is amplified as thymidine in the amplification product. MSP unmethylation (MSP(U)) specific primer pairs and MSP methylation (MSP(M)) specific are exemplified herein. For example, amplification primer pairs useful for such a method include, for example, a primer pair as set forth in SEQ ID NOS:42 and 43, which are methylation specific primers useful for detecting methylation of a GATA-5 gene; and a primer pair as set forth in SEQ ID NOS:40 and 41, which are unmethylation specific primers useful for detecting a lack of methylation of a GATA-5 gene 5' regulatory region (see Table 3). In view of the methylation-specific and unmethylation-specific primer pairs exemplified in Table 3, and the availability of nucleotide sequences comprising portions of target genes such as those disclosed herein, it will be recognized that additional methylation-specific and unmethylation-specific primer pairs useful for amplification of a methylated or an unmethylated GATA-4, GATA-5, TFF1, TFF2, TFF3, inhibin α, and/or Dab2 gene, readily can be made.

Accordingly, in one aspect, MSP is used for detecting the amount or distribution of uracil residues in a bisulfite ion treated target genes following alkaline treatment. Such a method can be performed by contacting the gene sequence with a first amplification primer pair and a second amplification primer pair under conditions suitable for amplification, wherein the first amplification primer pair comprises a forward primer and a reverse primer, and at least one primer of the first primer pair comprises an oligonucleotide that selectively hybridizes to a nucleotide sequence of the target gene that contains uracil residues, and wherein the second amplification primer pair comprises a forward primer and a reverse primer, and both primers of the second primer pair selectively hybridize to a target gene containing cytosine residues, but not to a target gene sequence containing uracil residues, and wherein an amplification product, if any, generated by the first primer pair has a first length, and an amplification product, if any, generated by the second primer pair has a second length, which is different from the first length, whereby the length of the amplification products is indicative of the amount or distribution of uracil residues and, therefore, of methylation of cytosine residues in CpG dinucleotides in the target gene of the test cell.

The amount or distribution of uracil residues also can be detected by contacting the 5' regulatory region of the gene with a first amplification primer pair and a second amplification primer pair under conditions suitable for amplification, wherein the first amplification primer pair comprises a forward primer and a reverse primer, wherein at least one primer of the first primer pair comprises an oligonucleotide that selectively hybridizes to a nucleotide sequence of the 5' regulatory region of the gene containing uracil residues, and wherein the second amplification primer pair comprises a forward primer and a reverse primer, wherein both primers of the second primer pair selectively hybridize to a nucleotide sequence of the 5' regulatory region of the gene containing cytosine residues, but not to a corresponding nucleotide sequence of the 5' regulatory region of the gene containing uracil residues, and wherein an amplification product, if any, generated by the first primer pair has a first length, and wherein an amplification product, if any, generated by the second primer pair has a second length, which is different from the first length, whereby the length of the amplification products is indicative of uracil residues and, therefore, methylation of cytosine residues in CpG dinucleotides in the 5' regulatory region of the gene, thereby detecting methylation silencing of the gene of the test cell.

Methylation silencing of a gene in a cell exhibiting or suspected of exhibiting unregulated growth (e.g., a gene associated with a cancer) also can be identified by contacting a test cell with a demethylating agent, and detecting increased expression of an RNA encoded by the gene as compared to a level of expression of the RNA in a test cell not contacted with a demethylating agent. Such a method can further include detecting methylation, if any, of cytosine residues in a CpG dinucleotide in a CpG island of the 5' regulatory region of the gene in a corresponding cell exhibiting regulated growth, or an extract of the corresponding cell The demethylating agent can be a methyltransferase inhibitor such as DAC. Increased expression of an RNA can be detected using any method for detecting RNA, including, for example, northern blot analysis, a reverse transcription-polymerase chain reaction assay, or selective hybridization to an array of nucleotide sequences as disclosed herein. Accordingly, the methods of the invention can be performed in a high throughput format, wherein the test cell, or extract of the test cell, comprises one of a plurality of test cells, or extracts of the test cells, or a combination thereof; and each of the test cells, or extracts of the test cells, of the plurality is the same or different, or a combination thereof.

In adapting the methods of the invention to a high throughput format, the test cells, or extracts of the test cell, can be arranged in an array, which can be an addressable array, on a solid support such as a microchip, a glass slide, or a bead, and the cells (or extracts) can be contacted serially or in parallel with an oligonucleotide probe or primer (or primer pair) as disclosed herein. Samples arranged in an array or other reproducible pattern can be assigned an address (i.e., a position on the array), thus facilitating identification of the source of the sample. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays. Conveniently, cells or extracts at a position in the array can be contacted with two or more oligonucleotide probes or primers (or primer pairs), wherein the oligonucleotides are differentially labeled or comprise a reaction that generates distinguishable products, thus providing a means for performing a multiplex assay. Such assays can allow the examination of one or more, particularly 2, 3, 4, 5, 10, 15, 20, or more genes to identify epigenetically silenced genes in a test cell. Further, samples can be examined using a multiplex format, wherein two or more genes (e.g., GATA-4 and GATA-5) are examined in a single reaction, and/or in which one or more genes is examined using a methylation-specific primer pair and an unmethylation-specific primer pair.

Oligonucleotides useful as probes or primers for identifying an epigenetic silenced gene (or the absence thereof) are provided. The term "oligonucleotide", "polynucleotide", or "nucleic acid molecule" is used broadly herein to mean a sequence of two or more deoxyribonucleotides or ribonucleotides that are linked together by a phosphodiester bond. The term "gene" also is used herein to refer to a polynucleotide sequence contained in a genome. It should be recognized, however, that a nucleic acid molecule comprising a portion of a gene can be isolated from a cell or can be examined as genomic DNA, for example, by a hybridization reaction or a PCR reaction. Thus, while in a genome, it may not always be clear as to a specific nucleotide position where a gene begins or ends, for purposes of the present invention, a gene is considered to be a discrete nucleic acid molecule that includes at least the nucleotide sequence the 5' regulatory region containing CpG islands to be examined for methylation status.

For convenience of discussion, the term "oligonucleotide" is used herein to refer to a polynucleotide that is used as a probe or primer, whereas the term "polynucleotide" or "nucleic acid molecule" is used more broadly to encompass any sequence of two or more nucleotides, including an oligonucleotide. As such, it should be recognized that the various terms used herein to conveniently distinguish different nucleic acid molecules. The term "oligonucleotide" or "polynucleotide" or the like include RNA and DNA, which can be a gene or a portion thereof, a cDNA, a synthetic polydeoxyribonucleic acid sequence, or the like. Generally, an oligonucleotide or polynucleotide can be single stranded or double stranded, as well as a DNA/RNA hybrid, although it will be recognized that the strands of a double stranded oligonucleotide that is to be used as a probe or primer will be separated, for example, by heating a solution containing the oligonucleotide above the melting temperature of the particular oligonucleotide.

The terms "oligonucleotide", "polynucleotide", and the like as used herein include naturally occurring nucleic acid molecules, which can be isolated from a cell, as well as fragments thereof as produced, for example, by a restriction endonuclease digestion, and synthetic molecules, which can be prepared, for example, by methods of chemical synthesis or by enzymatic methods such as by PCR. In various embodiments, an oligonucleotide or polynucleotide as disclosed herein can contain nucleoside or nucleotide analogs, and/or a backbone bond other than a phosphodiester bond, for example, a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994); Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium, a cell or in a living subject, since the modified polynucleotides can be designed to be less (or, if desired, more) susceptible to degradation.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide (or oligonucleotide) also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). As such, the polynucleotide can be prepared using a method such as conventional phosphotriester and phosphodiester methods, including, for example, an automated method such as that using diethylphosphoramidites (see Beaucage et al., *Tetrahedron Lett.*, 22:1859-1862, 1981), or a method whereby the oligonucleotides are synthesized on a modified solid support (see U.S. Pat. No. 4,458,066).

An oligonucleotide, which can selectively hybridize to a target nucleic acid molecule and can be used as a reagent for detecting expression and/or methylation (or lack of methylation; "unmethylation") of a gene, is designed to selectively hybridize to a nucleotide sequence within about 2000 nucleotides upstream (5') or downstream (3') of the target gene, and generally within about 1000 nucleotides of the region comprising the CpG island that is to be examined for cytosine methylation, usually within about 500 nucleotides of the site to be examined. In addition, as indicated above, an oligonucleotide of the invention, or useful in a method of the invention, is at least about 12 nucleotides in length, generally at least about 14 or 15 nucleotides in length, usually at least about 18 to 20 nucleotides, and can be about 25, 30, 35 or more nucleotides in length, such that it can selectively hybridize to a target nucleic acid molecule. It will be recognized that the length of the oligonucleotide will depend, in part, on the target gene. For example, when the target gene is one of a family of closely related genes having regions of substantial sequence similarity, a longer oligonucleotide can be used to assure selective hybridization to the target gene and minimal, if any, cross-hybridization to the related gene sequence(s).

The oligonucleotides are designed to be substantially complementary to at least one strand of a double stranded nucleic acid molecule corresponding to a genomic locus (or to each of both strands where an intervening sequence is to be amplified) and, where they are to be used for differentiating methylated from unmethylated cytosine residues, will include the appropriate guanine or cytosine residues, as discussed above. Oligonucleotides of the invention are exemplified by amplification primer pairs useful 1) for RT-PCR of a nucleotide sequence of a target gene; 2) for methylation specific or unmethylation specific amplification of a nucleotide sequence of a target gene; or 3) for bisulfite PCR.

The present invention also relates to a kit, which contains at least one isolated oligonucleotide useful for detecting a methylated or unmethylated GATA-4, GATA-5, TFF1, TFF2, TFF3, Dab2 and/or inhibin α gene, including, for example, a plurality of such isolated oligonucleotides. In one embodiment, a plurality of isolated oligonucleotides of a kit of the invention includes at least one amplification primer pair (i.e., a forward primer and a reverse primer), and can include a plurality of amplification primer pairs, including, for example, amplification primer pairs as set forth in SEQ ID NOS:10 to 71 (e.g., SEQ ID NOS:10 and 11, 12 and 13, 14 and 15, etc.). As such, a kit of the invention can contain, for example, one or a plurality of methylation specific amplification primer pairs, unmethylation specific amplification primer pairs, or a combination methylation specific amplification primer pairs and unmethylation specific amplification primer pair, including methylation specific primer pairs and unmethylation specific primer pairs useful for amplifying a methylated form or an unmethylated form of a particular gene that is known to be or suspected of being methylation silenced in one or more types of cancer cells.

A kit of the invention can further include additional reagents, which can be useful, for example, for a purpose for which the oligonucleotides of the kit are useful. For example, where a kit contains one or a plurality of methylation specific and/or unmethylation specific amplification primers, the kit can further contain, for example, control polynucleotides, which can be methylated or unmethylated; one or more reagents that modify methylated cytosine residues, and/or one or more reagents for performing an amplification reaction. Where the kit contains one or plurality of oligonucleotides that selectively hybridize to a methylated or to an unmethylated gene sequence, the kit can further contain, for example, a methylation sensitive restriction endonuclease. A kit of the invention also can contain at least a second primer pair, which can, but need not, be one of the above listed primer pairs, and can be useful, for example, for a nested amplification reaction. Such additional primer pairs can be designed based on the expected sequence of the amplified portion of the target gene using the sequence information available in the relevant GenBank™ Acc. No. for the target gene.

In one embodiment, a kit of the invention contains a methylation specific primer pair and an unmethylation specific primer pair, which are specific for the same target gene (e.g., SEQ ID NOS:40 and 41, and 42 and 43, which are specific for unmethylated and methylated GATA-5, respectively; see Table 3), thus allowing a user of the kit to determine whether a particular target gene is methylated or unmethylated. In another embodiment, the kit contains a plurality of such methylation specific and unmethylation specific primer pairs, thus allowing a user to determine the methylation of one or more target genes. For example, such a kit can contain a methylation-specific and/or unmethylation-specific primer pair useful for determining whether the 5' regulatory region of the GATA-S gene and, as desired, one or more GATA-5 target genes (e.g., Dab2, or TFF1) is methylated or unmethylated. Additional combinations of methylation and/or unmethylation specific primer pairs can be determined based on the present disclosure, thus providing kits that allow a determination of the methylation status of different genes. Such a kit can further contain a primer pair that includes oligonucleotides that selectively hybridize to an expected amplification product generated using the methylation specific or unmethylation specific primer pair, thus providing reagents useful for performing a nested amplification procedure.

A kit of the invention also can contain a detectable label that can be linked to or incorporated into an oligonucleotide of the kit, or a plurality of different detectable labels such that, depending the needs of the user, can be selected for a particular use, and, if desired, reagents for linking or incorporating the detectable label into the oligonucleotide. Alternatively, or in addition, the kit can contain one or more reagents useful for performing a hybridization reaction such that selective hybridization conditions readily are attained; and/or can contain one or more standard nucleic acid molecules, for example, a standard target GATA-5 nucleotide sequence that contains methylated cytosine residues corresponding the region to which the oligonucleotide is designed to selectively hybridize, or a standard target GATA-5 nucleotide sequence that contains unmethylated cytosine residues corresponding to the target sequence, or a combination thereof. Such standards provide several advantages, including, for example, allowing a confirmation that a reaction using a test cell, or extract thereof, functioned properly, or allowing for comparisons among samples examined at different times or collected from different sources. The kit also can contain one more oligonucleotides that selectively hybridize to GATA-6, which is not methylated in cancer, thus providing a negative control.

Where a kit contains one or more oligonucleotides useful for performing a primer extension (or amplification) reaction, the kit can further include reagents for performing the selective hybridization reaction such that the oligonucleotide provides a substrate for the extension reaction; and/or one or more reagents for performing the primer extension (or amplification) reaction, for example, dNTPs, one or more of which can be detectably labeled or otherwise modified for conveniently linking a detectable label; one or a selection of polymerases; and/or one or more standard target nucleic acid molecules. Where a kit of the invention contains two or more oligonucleotides (or primer pairs) such as those exemplified herein or otherwise useful for practicing the methods of the invention, the kit provides a convenient source of reagents from which the skilled artisan can select one or more oligonucleotides (or primer pairs), as desired.

A role for GATA-4, GATA-5, and GATA-6 in GI tumor development is compelling. Many cancers involve varying degrees of failure to complete cell differentiation and, thus, manifest a phenotype of maturation arrest. The patterns of silencing of the GATA genes as disclosed herein fosters this situation. GATA-4, GATA-5, and GATA-6 play distinct roles in embryonic GI development and in differentiation of mature GI epithelium (14, 20, 24). Loss of the differentiation stimulus of GATA-4 and GATA-5, with concomitant retention of the proliferative stimulus of GATA-6, would predictably impede differentiation and, therefore, can have a distinct role in progression of cancers with this gene expression profile. Although it is not clear why cancer cells would exhibit simultaneous epigenetic silencing of both upstream activating transcription factors and multiple downstream candidate target anti-tumor genes, and no mechanism is proposed herein for such an event, there are several possible explanations. First, tight physiologic linkage may not exist in the GI tract between the transcription factors and the candidate downstream genes examined. As such, the disclosed epigenetic events may not be linked, but may arise independently. As discussed above, however, experimental evidence points to a regulatory significance of GATA proteins for activating the genes examined herein. Further, the potential for all of the genes to play a role in cancer suggests that any coordination between the transcriptional factors and activation of the downstream genes would have great ramifications for cancer progression.

Second, some of the gene silencing events that were detected can reflect normal states that transiently precede differentiation in proliferating and renewing GI cell epithelial compartments. This possibility is suggested by the methylation data for the TFF genes, which have no promoter CpG islands. Differential promoter methylation is not unusual in normal tissues for non-housekeeping genes with CpG poor rich promoters and, as such, the presence or absence of promoter methylation in such genes can accompany their different transcriptional status during differentiation (4). However, promoter CpG islands for most genes, as detected for GATA-4, GATA-5, inhibin α, and Dab2, generally are not methylated in normal cells regardless of expression status (4), and none was observed in the normal tissues examined herein.

Third, a summation of their epigenetic inactivation during tumor progression can result in a more powerful tumorigenic effect. Finding simultaneous mutations for each involved gene in the same tumor may be quite rare. However, in individual tumors, epigenetically silencing of multiple genes occurs (8), and this mode of gene inactivation, in which protein function is less permanently, and perhaps less completely, disrupted than is the case for mutational events, can inactivate complex anti-tumor gene networks. Selection of cells may involve any combination of sporadic epigenetic inactivation events, which facilitate evolution of a cancer. For the downstream gene events, silencing may partially blunt the transcriptional response to upstream activating factors; however, continued expression of GATA factors, and perhaps other transcription factors with which the GATA proteins partner (5, 42), can activate downstream genes despite their local promoter methylation (see Example 1). Thus, selection during tumorigenesis for inactivation of one or both of the upstream GATA-4 and GATA-5 genes would contribute to the downstream silencing events, providing a powerful selection for loss of function of a group of GATA regulated anti-tumor genes.

While genetic changes generally are not reversible, the present results demonstrate that multiple epigenetically silenced candidate anti-tumor genes can be simultaneously reactivated in single tumors. Epigenetic silencing of important genes can occur early in the progression of cancers (19, 43). As such, the present results indicate that reactivation of epigenetically silenced genes can provide a means for cancer prevention, as well as for therapeutic strategies. Accordingly, the present invention relates to a method of reducing or inhibiting unregulated growth of a cell exhibiting epigenetic silenced transcription of at least one GATA-4, GATA-5, TFF1, TFF2, TFF3, Dab2 and/or inhibin α gene, which is associated with a cancer. Such a method can be practiced, for example, by restoring expression of a polypeptide encoded by the epigenetic silenced gene in the cell, thereby reducing or inhibiting unregulated growth of the cell. Such expression also can be restored, for example, by contacting the cell with a demethylating agent (e.g., a methyltransferase inhibitor), a histone deacetylase inhibitor, or a combination thereof. Restoration of express also can be obtained by providing the cell with a polypeptide encoded by the methylation silenced gene, or, in the case of a methylation silenced downstream target gene in a cell also containing methylation silenced GATA-5, by providing the cell with GATA-5 or a polynucleotide encoding GATA-5.

In one embodiment, the epigenetic silenced gene is a methylation silenced gene, and the method includes contacting the cell with at least one demethylating agent, for example, DAC. In one aspect, the cell can be contacted with the demethylating agent in vitro, e.g., in a culture medium or other medium conducive to survival of the cell. If desired, the cell contacted with the demethylating agent further can be administered to a subject. In another aspect, the agent can be administered to subject such that the cell exhibiting unregulated growth is contacted with the agent.

In another embodiment, the method includes introducing a polynucleotide encoding the polypeptide into the cell, whereby the polypeptide is expressed from the polynucleotide, thereby restoring expression of the polypeptide in the cell. The polynucleotide can, but need not, be contained in a vector, e.g., a viral vector, and/or can be formulated in a matrix that facilitates introduction of the polynucleotide into a cell, e.g., liposomes or microbubbles. The polynucleotide can be introduced into a cell by contacting the cell with the polynucleotide ex vivo, in which case the cell containing the polynucleotide can, but need not, be administered to a subject. The polynucleotide also can be introduced into a cell by contacting the cell with the polynucleotide in vivo. Where the cell is characterized by having methylation silenced GATA-5 gene expression, and methylation silenced TFF1, Dab2 and/or inhibin α gene expression, the cell can be contacted with GATA-5, or an expressible polynucleotide encoding GATA-5, wherein the GATA-5 overrides the methylation silencing of the downstream TFF1, Dab2 and/or inhibin α gene.

The present invention also relates to a method for selecting a therapeutic strategy for treating a cancer patient. Such a method can be performed, for example, by identifying at least one methylation silenced GATA-4, GATA-5, TFF1, TFF2, TFF3, Dab2 and/or inhibin α gene associated with the cancer, according to a method as disclosed herein; and selecting an agent useful for restoring expression of one or more of the identified methylation silenced gene in cancer cells of the patient. For example, the selected agent can be a polynucleotide encoding the identified methylation silenced gene, for example, a polynucleotide encoding a polypeptide encoded by a GATA-4, GATA-5, TFF1, TFF2, TFF3, Dab2 and/or inhibin α gene, or a combination of such genes, or, where the cell is characterized by having methylation silenced GATA-5, TFF1, Dab2 and/or inhibin α gene expression, the cell can be contacted with GATA-5, or an expressible polynucleotide encoding GATA-5, wherein the GATA-5 effects its function(s) and further overrides the methylation silencing of the downstream TFF1, Dab2 and/or inhibin α gene. The selected agent for restoring expression of a methylation silenced gene also can be a demethylating agent such as DAC.

The present invention also provides a method for treating a cancer patient, wherein cancer cells in the patient exhibit epigenetic silenced expression of at least one GATA-4, GATA-5, TFF1, TFF2, TFF3, Dab2 or inhibin α gene, or a combination thereof. Such a method can be performed, for example, by restoring expression of one or more epigenetic silenced genes in cancer cells in the patient. For example, where at least one epigenetic silenced gene is a methylation silenced gene, the patient can be treated by administering a demethylating agent to the subject in an amount sufficient to restore expression of the methylation silenced gene(s) in cancer cells in the subject. Alternatively, or in addition, the patient can be treated by administering at least one polynucleotide encoding at least one polypeptide (e.g., GATA-5) encoded by one or more of the methylation silenced genes to the subject under conditions sufficient for expression of the at least one polypeptide in cancer cells in the subject. Where a polynucleotide is administered to the patient, the polynucleotide can be contained in a vector (e.g., a viral vector) preferably an expression vector, and/or can be formulated in a matrix that facilitates uptake of the polynucleotide by a target cancer cell (e.g., in a liposome).

The cancer to be treated according to a method of the invention can be any type of cancer. For example, where the cancer is a CRC and/or GC, the patient can be treated by restoring expression of the one or more epigenetic silenced genes. In one embodiment, a method is provided for treating a subject suffering from a CRC and/or GC, wherein cells associated with the cancer contain at least one methylation silenced GATA-4, GATA-5, TFF1, TFF2, TFF3, Dab2 or inhibin α gene. Such a method can be performed, for example, by administering an amount of an agent that restores expression of the methylation silenced gene(s) to the subject sufficient to restore expression of the methylation silenced gene(s) in cells associated with the cancer. The agent can be a polynucleotide encoding the at least one methylation silenced gene, for example, a polynucleotide encoding GATA-5, or can be a demethylating agent such as DAC. An agent useful for treating a subject suffering from a colorectal cancer, a gastric cancer, or both, can be contacted with cells of the cancer ex vivo, after which the cells can be administered back into the patient; or the agent can be administered to a site of the cancer cells in the patient.

As a result of methylation silenced transcription of one or more of GATA-4, GATA-5, TFF1, TFF2, TFF3, Dab2 and inhibin α in a cell, the gene product(s) is not present in the cell and, therefore, there is a loss of function associated with the absence of the encoded gene product(s). Accordingly, the methods of the invention are based on providing a cell that exhibits unregulated growth due to epigenetic silenced, particularly methylation silenced GATA-4, GATA-S, TFF1, TFF2, TFF3, Dab2 and/or inhibin α gene expression, with the polypeptide encoded by the methylation silenced gene(s), or, in some cases as disclosed herein, with a polynucleotide encoding GATA-5, thereby restoring expression of the methylation silenced genes and regulated growth of the cell. As disclosed herein, the polypeptide can be provided to the cell directly, can be expressed from an exogenous polynucleotide that is introduced into the cell and encodes the polypeptide, or by restoring expression of the endogenous methylation silenced gene in the cell. Upon restoring the polypeptide(s) to a cell exhibiting unregulated growth, characteristics generally associated with unregulated growth, including, for example, the ability to grow in soft agar, a lack of contact inhibited growth, or refractoriness to programmed cell death, are alleviated.

Expression of one or more methylation silenced GATA-4, GATA-5, TFF1, TFF2, TFF3, Dab2 and/or inhibin α gene can be restored, for example, by contacting the cells with a demethylating agent such as DAC, which, when incorporated into the genes during replication of the cell results in progeny cells containing unmethylated genes, which can be transcribed. The cells contacted with the demethylating agent can be cells in culture, wherein the demethylating agent is added to the cell culture medium in an amount sufficient to result in demethylation of the target genes, without being toxic to the cells. The cells in culture can be cells of an established cell line, or can be cells, which can be a mixed population of cells, that have been removed from a subject and are being contacted ex vivo, for example, to determine whether contact with the particular demethylating agent can restore expression of the target gene(s), and therefore, can be useful when administered to the subject. Such ex vivo treatment of the cells also can be useful for restoring expression of the target gene, after which the cells optionally can be expanded in culture and administered back to the subject. Such a method, as well as any of the methods of treatment as disclosed herein, can further include treatments otherwise known in the art as useful for treating a subject having the particular cancer, or that can be newly useful when used in combination with the present methods.

Cells exhibiting methylation silenced gene expression also can be contacted with the demethylating agent in vivo by administering the agent to a subject. Where convenient, the demethylating agent can be administered using, for example, a catheterization procedure, at or near the site of the cells exhibiting unregulated growth in the subject, or into a blood vessel in which the blood is flowing to the site of the cells. Similarly, where an organ, or portion thereof, to be treated can be isolated by a shunt procedure, the agent can be administered via the shunt, thus substantially providing the agent to the site containing the cells. The agent also can be administered systemically or via other routes as disclosed herein or otherwise known in the art.

A polypeptide, which is reduced or absent due to an epigenetic silenced gene, also can be provided to a cell by introducing a polynucleotide encoding the polypeptide into the cell, whereby the polypeptide is expressed from the polynucleotide in the cell. As such, the present invention provides methods of gene therapy, which can be practiced in vivo or ex vivo. For example, where the cell is characterized by methylation silenced transcription of the GATA-5 gene, a polynucleotide having a nucleotide sequence as set forth in GenBank™ Acc. No. NM_080473 (SEQ ID NO:2) can be introduced into the target cell. An advantage of introducing such a polynucleotide into a cancer cell is that, upon expression, GATA-5 can override, when present, methylation silenced TFF1, Dab2 and/or inhibin α gene expression.

The polynucleotide to be introduced into a cancer cell can include, in addition to polypeptide coding sequence, operatively linked transcriptional regulatory elements, translational regulatory elements, and the like, and can be in the form of a naked DNA molecule, which can be contained in a vector, or can be formulated in a matrix such as a liposome or microbubbles that facilitates entry of the polynucleotide into the particular cell. As used herein, the term "operatively linked" refers to two or more molecules that are positioned with respect to each other such that they act as a single unit and effect a function attributable to one or both molecules or a combination thereof. For example, a polynucleotide encoding GATA-5 can be operatively linked to a second (or more) coding sequence such that a chimeric polypeptide can be expressed from the operatively linked coding sequences. The chimeric polypeptide can be a fusion protein, in which the two (or more) encoded polypeptides are translated into a single polypeptide, i.e., are covalently bound through a peptide bond; or can be translated as two discrete peptides that, upon translation, can operatively associate with each other to form a stable complex. Similarly, a polynucleotide sequence encoding a desired polypeptide can be operatively linked to a regulatory element, in which case the regulatory element confers its regulatory effect on the polynucleotide similarly to the way in which the regulatory element would effect a polynucleotide sequence with which it normally is associated with in a cell.

A fusion protein generally demonstrates some or all of the characteristics of each of its polypeptide components, and, therefore, can be useful for restoring gene expression in the cell and can further provide additional advantages. For example, the fusion protein can include a polypeptide, which is otherwise reduced or absent due to epigenetic silencing of its encoding gene, operatively linked to a cell compartment localization domain such that expression of the fusion protein in a cell or loading of the cell with fusion protein allows translocation of the encoded polypeptide to the intracellular compartment such as the nucleus, in which it effects its activity. Cell compartmentalization domains, for example, are well known and include a plasma membrane localization domain, a nuclear localization signal, a mitochondrial membrane localization signal, an endoplasmic reticulum localization signal, and the like, as well as signal peptides, which can direct secretion of a polypeptide from a cell (see, for example, Hancock et al., *EMBO J.* 10:4033-4039, 1991; Buss et al., *Mol. Cell. Biol.* 8:3960-3963, 1988; U.S. Pat. No. 5,776,689 each of which is incorporated herein by reference). The fusion protein also can comprise a desired polypeptide operatively linked to a peptide that acts as a ligand for a receptor, a peptide useful as a tag for identifying a cell in which the polypeptide is expressed, or for isolating the fusion protein, or any other peptide or polypeptide of interest, providing the fusion protein has the protein activity of the desired polypeptide.

Peptide tags such as a polyhistidine tag peptide, e.g., His-6, which can be detected using a divalent cation such as nickel ion, cobalt ion, or the like; a FLAG epitope, which can be detected using an anti-FLAG antibody (see, for example, Hopp et al., *BioTechnology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione, are well known in the art, and provide a means of detecting the presence of a polypeptide operatively linked thereto. Such tags provide the additional advantage that they can facilitate isolation of the operatively linked polypeptide, for example, where it is desired to obtain the polypeptide in a substantially purified form, such a polypeptide also being useful for practicing methods of the invention.

A polynucleotide encoding a polypeptide otherwise encoded by a methylation silenced gene can be used alone, or can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and encoded polypeptide in a particular cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide encoding the desired polypeptide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

A tetracycline (tet) inducible promoter can be particularly useful for driving expression of a polynucleotide encoding a desired polypeptide. Upon administration of tetracycline, or a tetracycline analog, to a subject containing a polynucleotide operatively linked to a tet inducible promoter, expression of the encoded polypeptide is induced. The polynucleotide also can be operatively linked to tissue specific regulatory element, for example, a liver cell specific regulatory element such as an I-fetoprotein promoter (Kanai et al., *Cancer Res.* 57:461-465, 1997; He et al., *J. Exp. Clin. Cancer Res.* 19:183-187, 2000) or an albumin promoter (Power et al., *Biochem. Biophys. Res. Comm.* 203:1447-1456, 1994; Kuriyama et al., *Int. J. Cancer* 71:470-475, 1997); a muscle cell specific regulatory element such as a myoglobin promoter (Devlin et al., *J. Biol. Chem.* 264: 13896-13901, 1989; Yan et al., *J. Biol. Chem.* 276:17361-17366, 2001); a prostate cell specific regulatory element such as the PSA promoter (Schuur et al., *J. Biol. Chem.* 271:7043-7051, 1996; Latham et al., *Cancer Res.* 60:334-341, 2000); a pancreatic cell-specific regulatory element such as the elastase promoter (Ornitz et al., *Nature* 313:600-

602, 1985; Swift et al., *Genes Devel.* 3:687-696, 1989); a leukocyte specific regulatory element such as the leukosialin (CD43) promoter (Shelley et al., *Biochem. J.* 270:569-576, 1990; Kudo and Fukuda, *J. Biol. Chem.* 270:13298-13302, 1995); or the like, such that expression of the polypeptide is restricted to particular cell in an individual, or to particular cells in a mixed population of cells in culture, for example, an organ culture. Regulatory elements, including tissue specific regulatory elements, many of which are commercially available, are well known in the art (see, for example, InvivoGen; San Diego Calif.).

Viral expression vectors also can be particularly useful for introducing a polynucleotide into a cell, particularly a cell in a subject. Viral vectors provide the advantage that they can infect host cells with relatively high efficiency and can infect specific cell types. For example, a polynucleotide encoding a desired polypeptide can be cloned into a baculovirus vector, which then can be used to infect an insect host cell, thereby providing a means to produce large amounts of the encoded polypeptide. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, hepatitis virus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med.* 334:1185-1187 (1996), each of which is incorporated herein by reference).

A polynucleotide, which can be contained in a vector, can be introduced into a cell by any of a variety of methods known in the art (Sambrook et al., supra, 1989; Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. A particularly useful method comprises incorporating the polynucleotide into microbubbles, which can be injected into the circulation. An ultrasound source can be positioned such that ultrasound is transmitted to the tumor, wherein circulating microbubbles containing the polynucleotide are disrupted at the site of the tumor due to the ultrasound, thus providing the polynucleotide at the site of the cancer. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. A polynucleotide of the invention, or a vector containing the polynucleotide can be contained in a cell, for example, a host cell, which allows propagation of a vector containing the polynucleotide, or a helper cell, which allows packaging of a viral vector containing the polynucleotide. The polynucleotide can be transiently contained in the cell, or can be stably maintained due, for example, to integration into the cell genome.

A method of the invention also can be practiced by directly providing desired polypeptide to a cell exhibiting unregulated growth. The polypeptide can be produced and isolated, and formulated as desired, using methods as disclosed herein. The polypeptide can be contacted with the cell in vitro under conditions that result in sufficient permeability of the cell such that the polypeptide can cross the cell membrane, or can be microinjected into the cells. Where the desired polypeptide is contacted with a cell in situ in an organism, it can comprise a fusion protein, which includes a peptide or polypeptide component that facilitates transport across the cell membrane, for example, a human immunodeficiency virus (HIV) TAT protein transduction domain, and can further comprise a nuclear localization domain operatively linked thereto. Alternatively, or in addition, the polypeptide can be formulated in a matrix that facilitates entry of the polypeptide into a cell.

For administration to a living subject, an agent such as a demethylating agent, a polynucleotide, or a polypeptide useful for practicing a therapeutic method of the invention generally is formulated in a composition suitable for administration to the subject. Thus, the invention provides compositions containing an agent that is useful for restoring regulated growth to a cell exhibiting unregulated growth due to methylation silenced transcription of one or more genes. As such, the agents are useful as medicaments for use in treating a subject suffering from a pathological condition associated with such unregulated growth, as well as for use in preparing a medicament for administration to a subject suffering from the pathologic condition (e.g., CRC and/or GC).

Such compositions generally include a carrier that can is acceptable for formulating and administering the agent to a subject. Such acceptable carriers are well known in the art and include, for example, aqueous solutions such as water or physiologically buffered saline or other solvents or vehicles such as glycols, glycerol, oils such as olive oil or injectable organic esters. An acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of an acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second reagent such as a diagnostic reagent, nutritional substance, toxin, or therapeutic agent, for example, a cancer chemotherapeutic agent.

The agent can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful in a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580-2585 (1993), which is incorporated herein by reference). In addition, a polynucleotide agent can be introduced into a cell using, for example, adenovirus-polylysine DNA complexes (see, for example, Michael et al., *J. Biol. Chem.* 268:6866-6869 (1993), which is incorporated herein by reference).

The route of administration of the composition containing the therapeutic agent will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are disclosed herein or otherwise known in the art (see, for example, Blondelle et al., supra, 1995; Ecker and Crook, supra, 1995). In addition, a polypeptide agent can be prepared using D-amino acids, or can contain one or more domains based on peptidomimetics, which are organic molecules that mimic the structure of a domain; or based on a peptoid such as a vinylogous peptoid.

A composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of an agent to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the composition to treat a pathologic condition in a subject depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual nontoxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The following examples are intended to illustrate but not limit the invention.

EXAMPLE 1

Methylation Silenced Genes Associated with Colorectal Cancer and Gastric Cancer

This example demonstrates that GATA-4 and GATA-5, as well as several downstream target genes regulated by GATA-4 and GATA-5 are methylation silenced in cancer cells, and that expression of GATA-5 in such cells can override the epigenetic silencing of methylation silenced downstream target genes.

Cell Lines and Tissue Samples

Six colorectal cancer (CRC) cell lines (RKO, HCT116, DLD-1, HT29, LoVo, and SW480), 1 gastric carcinoma (GC) cell line, AZ-521, 45 primary CRC samples, and 27 primary GC samples were examined. All primary normal and neoplastic tissues were collected under clinical research guidelines at all participating institutions.

Drug Treatment of Cells and RNA Extraction

The CRC and AZ521 cell lines were grown in DMEM, MEM or McCoy's medium supplemented with 10% fetal bovine serum, penicillin and streptomycin. For demethylation studies, cells were treated daily with 5 pM 5-aza-2'deoxycytidine (DAC; Sigma Chemical Co.; St. Louis Mo.) for 48 hr (41). AZ521 and HCT116 cells also were treated with the histone deacetylase inhibitor, TSA (Wako), alone, or with a combination of DAC plus TSA (41; 6). Total RNA was isolated using the TRIZOL reagent (Invitrogen Corp.; Carlsbad Calif.).

RT-PCR

For RT-PCR, 2 µg of total RNA was reverse transcribed using the SUPERSCRIPT reverse transcription kit (Invitrogen); all genes were amplified with multiple cycle numbers (28-35 cycles) for obtaining semi-quantitative differences in their expression levels. Primer pairs for GATA-1 to GATA-6 and for the GATA-5 target genes are shown in Table 2 (see, also, Bai et al., *Mol. Carcinog.* 28:184-188, 2000, which is incorporated herein by reference). Annealing was performed at the indicated temperatures, and PCR was performed for the indicated number of cycles (Table 2, below). PCR conditions were as follows: first denature, 95° C., 5 min; denature, 95° C., 1 min; anneal, temperature shown in Table 2 (° C.), 1 min; extension, 72° C., 1 min; final extension, 72° C., 10 min.

Methylation Analyses

DNA extraction, bisulfite treatment, DNA sequencing (Johns Hopkins University School of Medicine Biosynthesis and Sequencing Facility, Department of Biological Chemistry), and methylation specific PCR (MSP) were performed as previously described (7, 17). Primers for methylation specific PCR (MSP) and unmethylation specific PCR are shown in Table 3 (below). Primers for bisulfite sequencing are shown in Table 4 (below).

Recombinant Adenovirus Generation and Infection Procedure

Full length GATA-5 was amplified from human gastric cancer cDNA according to GenBank™ sequences (GenBank™ Acc. Nos. NM_080473 (SEQ ID NO:2) and AL499627) and subcloned into a pAdTrack-CW™ shuttle plasmid vector (16). GenBank™ Acc. No. NM_080473 provides the cDNA (SEQ ID NO:2) and polypeptide sequences of GATA-5. GenBank™ Acc. No. AL499627 provides a cloned region of human chromosome 20 that contains the gene encoding GATA-5, including two CpG islands. Viral titer was determined by plaque assay in low passage 293 cells, and infection was performed using doses of 0.4 plaque-forming units (pfu)/cell in HCT116, 8 pfu/cell in RKO, and 4 pfu/cell in AZ521 cells to give at least 70% GFP reactive cells with minimal to no cytotoxicity.

Immunoblotting

For examination of GATA-5 protein expression, adenovirus infected cells were harvested after 48 hr or 72 hr, lysed in sample buffer (LB broth, DTT and benzenesulfonyl fluoride), and western blot analysis was performed on 5 μg of cell lysate using a goat GATA-5 polyclonal antibody (1:200 dilution; Santa Cruz Biotechnology). For examination of TFF1 expression, western blot analysis was performed with 40 μl of cell culture media using a mouse anti-pS2 peptide (1:150 dilution; Zymed Laboratories, CA).

Epigenetic Silencing of GATA-4 and GATA-5 in CRC and GC

GATA-4, GATA-5 and GATA-6 expression was examined in gastrointestinal cancer cell lines. GATA-4, GATA-5 and GATA-6 expression levels were examined by RT-PCR in seven cancer cell lines (colon cancer cell lines RKO, DLD1, HCT116, HT29, LoVo, and SW480; and gastric cancer cell line AZ521) with or without (mock) treatment with 5'-aza-2'-deoxycytidine (DAC) and in normal colonic mucosa (NC) and peripheral blood lymphocytes (PBL). GAPDH expression was used for an internal loading control for the RT-PCR. Gastric cancer cells, AZ521, were treated with low dose DAC alone, TSA alone, or a combination of these two drugs (A/T), or were mock treated, and examined by RT-PCR. GATA-4 and GATA-5 expression were examined in wild type (WT) HCT116 colon cancer cells, and two clones each of these cells in which both alleles of DNA methyltransferase 1 (DNMTI-KO), DNMT 3b (DNMT3b-KO), or both DNMTs were knocked out (21). PCR products recognizing unmethylated and methylated CpG sites were analyzed in 2.5% agarose gels stained by ethidium bromide.

Semi-quantitative RT-PCR revealed that GATA-1, GATA-2, and GATA-3 were expressed in lymphocytes, but not in normal colon. GATA-4, GATA-5, and GATA-6 were all expressed in normal colon, while only GATA-6 was expressed in lymphocytes (Table 1, below). GATA-1 was not expressed in any of the cancer cell lines, whereas GATA-6 was expressed in each of the cancer cell lines. GATA-2 was expressed in all the cell lines except RKO CRC cells, and GATA-3 was absent from RKO and LoVo CRC cells. Four of 6 CRC lines and the GC line did not express GATA-4; all of the cell lines except the LoVo CRC cells lacked GATA-5, and 5 of the 7 lines lacked both GATA-4 and GATA-5 (Table 1).

The demethylating agent, DAC, was used to initially study the epigenetic status of GATA-4, GATA-5, and GATA-6 in each of the cell lines (Table 1, below). Each basally silent GATA gene, except GATA-1, which is not expressed in normal colon, was re-expressed upon DAC treatment. The silenced GATA-4 and GATA-5 genes had characteristics of hypermethylated tumor suppressor genes (41, 6) in that treatment with the histone deacetylation inhibitor, TSA, alone, failed to reactivate these genes, whereas TSA was synergistic in reactivating expression of these genes when applied with a low dose of DAC. Expression of GATA-4 and GATA-5 was restored in HCT 116 CRC DKO cells, in which two key DNA methyltransferases, DNMT1 and DNMT3b, were biallelically disrupted with resultant virtual abolition of DNA methyltransferase activity (34); there was very minor expression of GATA-4 in HCT 116 cells in which DNMT1, alone (35), was knocked out.

Figure 1B:
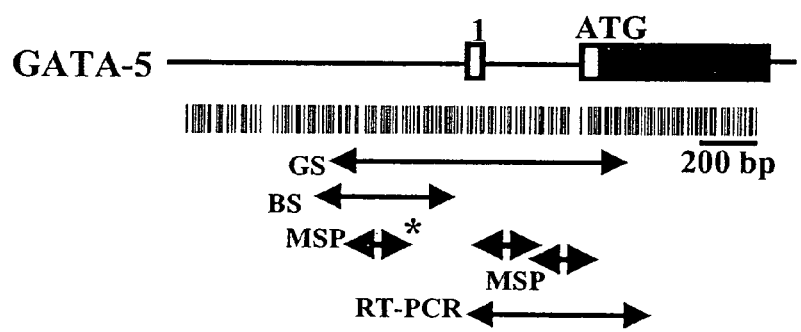
Figure 1C:
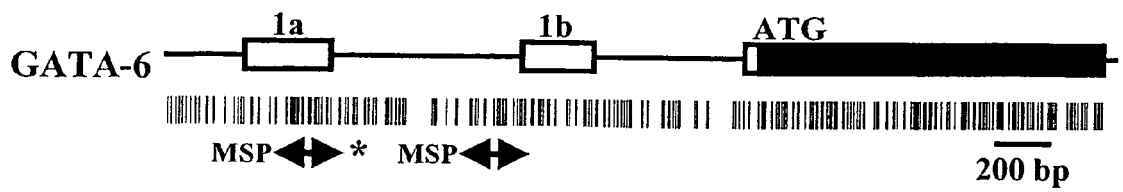
Figure 2C:
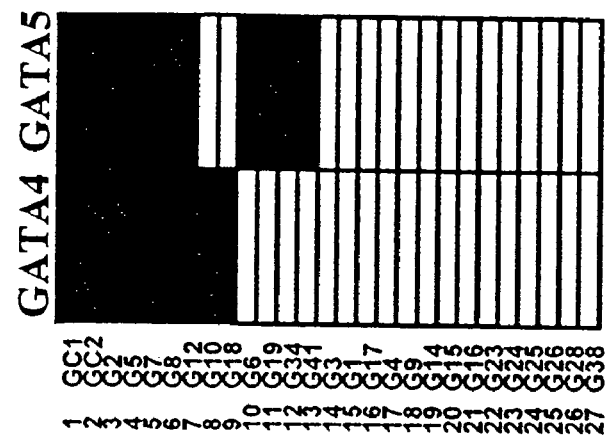
FIGS. 2A to 2C show the results of methylation analysis of GATA-4 and GATA-5 in non-cultured normal and neoplastic GI samples.
Figure 2B:
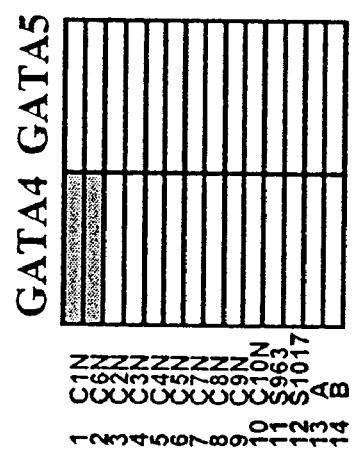
Figure 2A:
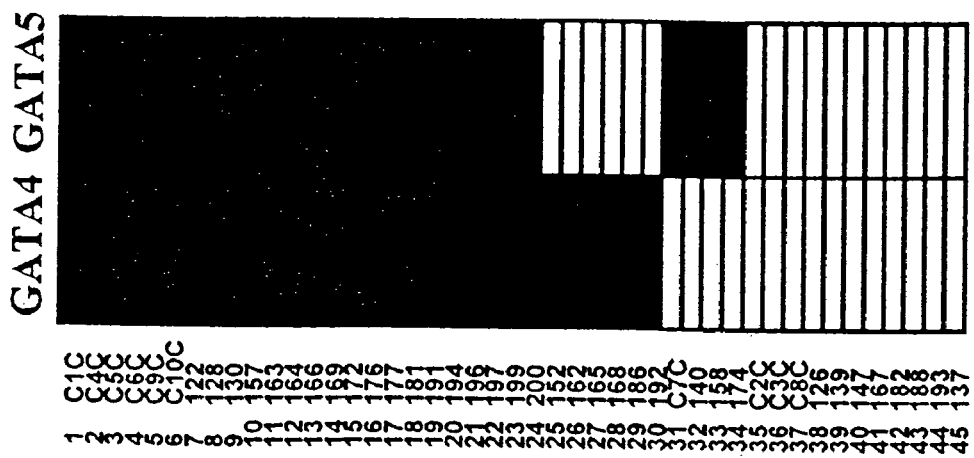

GATA-4 and GATA-55 Promoter CpG Island Methylation in Cultured and Primary CRC and GC Cells The promoter methylation status of GATA-4, GATA-5 and GATA-6 was examined. RT-PCR studies combined with EST identification in database searches clarified the 5' structure of each of the genes and identified CpG islands associated with the most 5' promoter regions of each (FIG. 1). MSP analyses revealed these islands to be typical in having a non-methylated status regardless of the gene expression state (4) in normal lymphocytes and normal colon from patients without cancer. GATA-4 had a weak methylation signal in 2 normal colon mucosa samples from patients with cancers in which the gene is hypermethylated, as detailed below, but was not methylated in 12 other normal samples from patients with CRC (FIGS. 2A and 2B). Methylation of GATA-5 was not observed in any normal sample (FIGS. 2A and 2B), and neither gene was methylated in 5 normal gastric mucosa samples examined.

In contrast to the above normal patterns, the promoters of GATA-4 and GATA-5 were abnormally methylated in cultured gastrointestinal (GI) cancers in which these genes are basally silent, while GATA-6 was unmethylated in all of these same cultures (Table 1). In the CRC HCT116 cells, the wild type cells contained only a signal for methylated alleles of GATA-4 and GATA-5, while only unmethylated alleles were found in the DKO cells. In addition, GATA-4 and GATA-5 frequently were hypermethylated in primary tumors, with strong MSP methylation signals in 30/45 (66.7%) and 28/44 (63.6%) primary CRC tissues, respectively; both genes were hypermethylated in 24 of the tumors (see FIG. 2A). Of 27 GC tissues examined, 9 (33.3%) were GATA-4 methylation-positive, 11 (40.7%) were positive for GATA-5, and 7 had hypermethylation of both genes (FIG. 2C).

Figure 3:
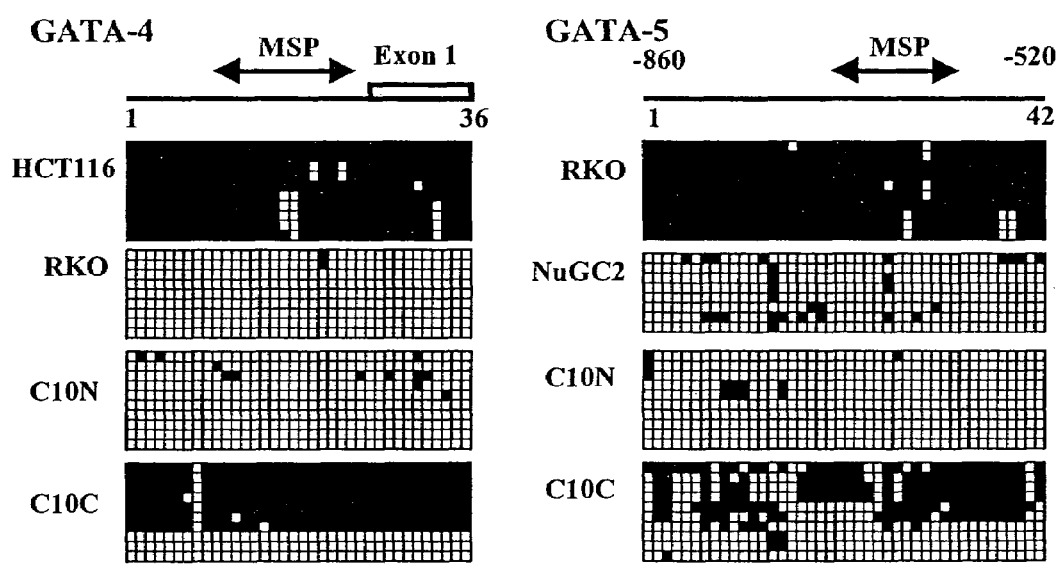
FIG. 3 provides an analysis of sodium bisulfite DNA sequencing of GATA-4 and GATA-5 in colorectal (RKO and HCT116) and gastric (NuGC2) cancer cell lines and in various non-cultured GI tissue samples. Each horizontal row of squares represents analysis, in a single clone of bisulfite treated DNA, of 36 (GATA-4) or 42 (GATA-5) CpG sites contained in the region shown. Filled and open squares represent methylated and unmethylated CpG sites, respectively. GATA-negative expression cell lines (GATA-4 in HCT116 and GATA-5 in RKO) show densely methylated clones, whereas expression-positive cells (GATA-4 in RKO and GATA-5 in NuGC2 gastric cancer cells) had predominantly unmethylated clones. A primary colon cancer (Case C10C) had predominantly methylated clones of GATA-4 and GATA-5 and normal colon mucosa from the same patient (C10N) had unmethylated clones.

In selected samples, MSP results were verified by bisulfite sequencing (FIG. 3). GATA expression negative cultured tumor cells, including HCT116 (GATA-4 expression negative) and RKO GATA-5 expression negative), and methylation positive primary CRC samples showed dense methylation of the promoter CpG islands, whereas expression positive cultured tumor cells, including RKO (GATA-4 expression positive) and NuGC-2 (GATA-5 expression positive GC line (3)), and normal colon samples, showed only scattered methylation within the examined regions. One of the normal colon samples with a weak MSP methylation signal for GATA-4 (C1N) was hypermethylated only in the 5' and 3' borders of the promoter CpG island. The primary colon cancer, C10, shown to be hypermethylated for the promoter regions of GATA-4 and GATA-5 by MSP, was densely methylated for most alleles as analyzed by bisulfite sequencing (FIG. 3).

GATA Genes and Downstream Targets are Epigenetically Silenced in GI Cancers

The question of how GATA gene silencing correlates with expression of candidate downstream genes, which are up-regulated by these transcription factors and some of which are speculated to act as putative anti-tumor genes, was examined. One such group of downstream target genes, the TFF genes, are predominantly expressed in gastric (44) and colonic epithelium (40) and encode secreted proteins that help guide epithelial cells properly during repair of damaged GI epithelium (25, 9). TFF1 (also known as pS2) is a tumor suppressor gene. Approximately 30% of TFF1 knockout mice develop gastric adenomas and carcinomas (25), and occasional mutations, allelic deletions and reduced expression occur in human primary gastric cancers (12, 33). TFF1 and TFF2 (1) are up-regulated by the CRC prevention agents, non-steroidal (NSAIDS), indomethacin, and aspirin (2). As disclosed herein, TFF1, TFF2 and TFF3, while not expressed in normal lymphocytes, were all expressed in normal colon; TFF1 expression was absent from 4 of 7 cancer cell lines, TFF2 expression was absent from 3 of 7 cancer cell lines, and TFF3 expression was absent from 3 of 7 cancer cell lines (Table 1).

GATA-1 and GATA-4 can bind and up-regulate the promoter of the inhibin α gene, a member of the TGF-β superfamily (10, 21) that induces gonadal sex cord-stromal tumors when disrupted in mice (27). Expression of inhibin α was not detected in normal lymphocytes or in colon. A SAGE tag and EST (GenBank™ Acc. No. BM987739) exist from normal colon mucosa; this gene was expressed in some of the tumor cell lines (Table 1), but expression was absent from 2 of the 7 cancer lines studied, and the gene was barely to poorly expressed in 2 others (Table 1).

Disabled-2 (Dab2) is a candidate tumor suppressor gene reported to be directly activated by GATA-6 (30). Past work examining activation of Dab2 has been confusing in light of most recent studies (37), which suggest that the true promoter region and exon 1 for this gene are at least 14 kilobases upstream from the previously described promoter. The present results clarify the role of this newly identified region and link it to expression of the gene. Dab2 fails to express in a very high frequency of breast and ovarian cancers, and its absence has been correlated to ability of epithelial cancer cells to grow out of context to the basement membrane (38). As disclosed herein, Dab2 was expressed in normal colon and lymphocytes; however, using RT-PCR primers for the internal coding region and primers linking the newly reported upstream first exon to this coding area, expression was absent from one (RKO cells) of the CRC lines (Table 1).

In considering the pattern for basal expression of all of the candidate genes for GATA regulation (Table 1), RKO cells lacked expression of 5 of the 6 genes; HCT 116 cells lacked expression of 4 of the 6 genes, and AZ521 cells lacked expression of 3 of the 6 genes. Despite evidence that GATA factors can up-regulate the expression for all the downstream genes studied, simple absence of GATA-4 or GATA-5 expression does not appear to account for loss of downstream gene expression. For example, cell lines HCT116, DLD1, HT29, SW480, and AZ521 all have loss of GATA-4 and GATA-5 expression. Yet TFF1 is not expressed in HCT116, SW480, and AZ251, but is expressed in DLD1 and HT 29 (Table 1). TFF2 is not expressed in HCT 116 and AZ251, but is expressed in DLD1, HT29, and SW480. Similar discrepancies are apparent in Table 1 for others of the genes.

Despite this lack of coordination between expression of upstream and downstream genes, silencing of all the downstream genes appears to be, as for GATA-4 and GATA-5, under epigenetic regulation in multiple of the GI cancer cell lines. When the cells were treated with DAC, each downstream gene was activated in virtually every cell line in which the gene lacked basal expression, and in many instances (TFF1, TFF3, inhibin α) a low basal expression was further increased (see Table 1). Two exceptions occurred in cell lines RKO and AZ521, where TFF2 did not re-express after DAC treatment (Table 1). As discussed below, the promoter region for TFF2 appeared to be either homozygously mutated and/or deleted from the genomes of the RKO and AZ521 cell lines. In a CRC cell line, HCT116, where the TFF2 promoter is present, the gene was readily activated by DAC (Table 1). Also, all four silent genes in wild type HCT116 cells, including TFF1, TFF2, TFF3, and inhibin α, were re-expressed in the HCT116-DKO cells.

Figure 4A:
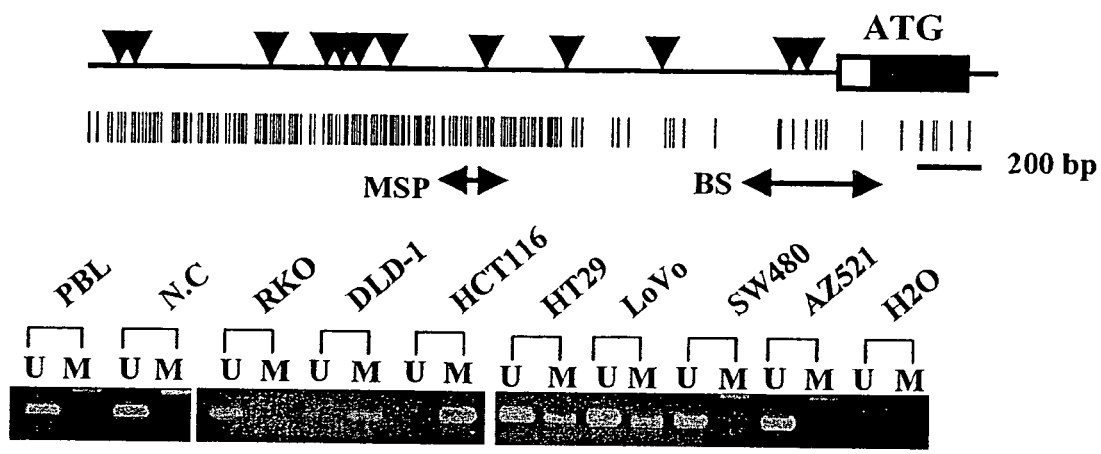
FIGS. 4A and 4B show the methylation status of GATA downstream target genes in cultured colon and gastric cancer cells and normal tissues
Figure 4B:
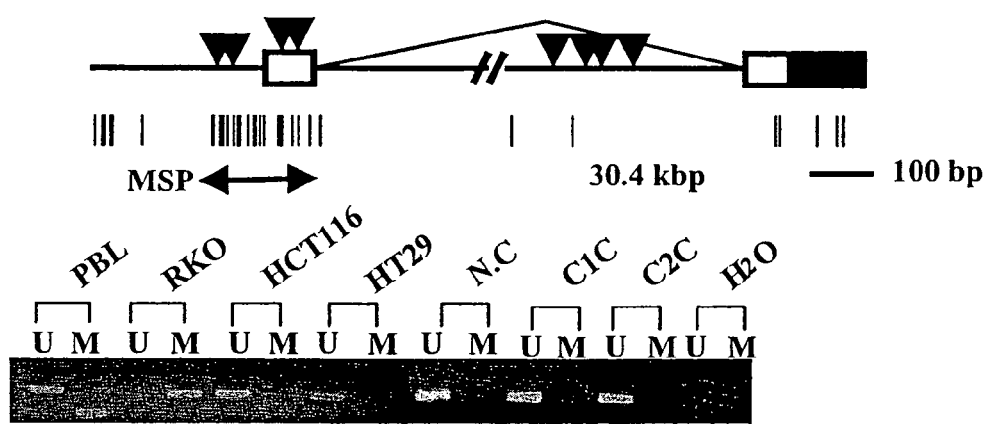

As for GATA-4 and GATA-5, expression of the downstream genes was associated, in most cases, with methylation of their promoter regions, although several different types of methylation patterns were involved. Basal silencing in cancer cells of the candidate GATA target genes, inhibin α and Dab2, appears to involve classic tumor specific hypermethylation of promoter CpG islands. The initial region defined as the promoter for inhibin α (FIG. 4A) was CpG poor, contained only two GATA binding motifs (36), and was methylated in normal and tumor cell lines regardless of expression status. However, a typical CpG island that contains multiple additional GATA binding sites was identified approximately 700 bp upstream (FIG. 4A). The methylation status of this CpG island correlated exactly with expression status, being unmethylated in normal colon or lymphocytes; unmethylated, or only partially methylated, in cancer lines, which basally express inhibin α; and fully methylated in the three lines in which the gene was basally silent (Table 1; see, also, FIG. 4A). The upstream promoter region and untranslated exon 1 of Dab2 (36) had an associated CpG island, which in current databases lies about 30 kilobases from exon 2 (FIG. 4B). By MSP analysis, this island was unmethylated in normal colon and lymphocytes and in the six cell lines which express the gene, but fully methylated in RKO cells in which this gene is basally silent and reactivated following DAC treatment (Table 1; FIG. 4B).

Figure 5A:
FIGS. 5A to 5D show the methylation status of the trefoil genes, TFF1, TFF2 and TFF3 in cultured colon cancer cells.
Figure 5B:
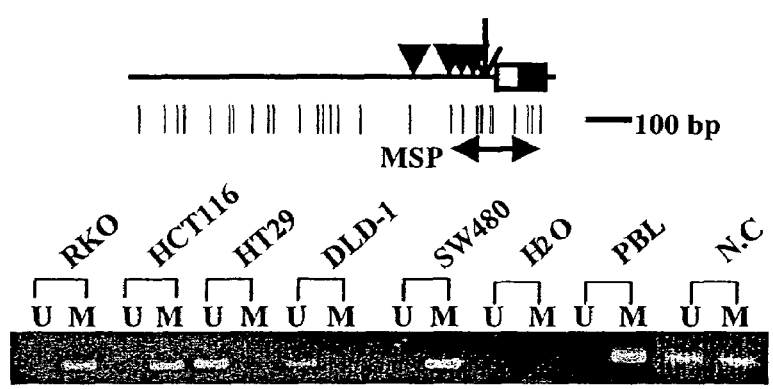
Figure 5C:
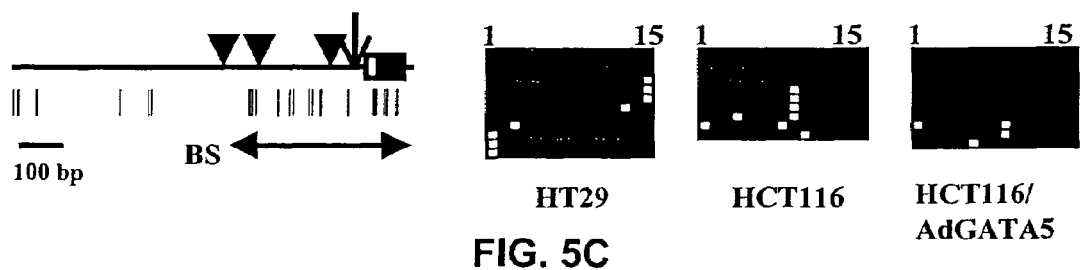
Figure 5D:
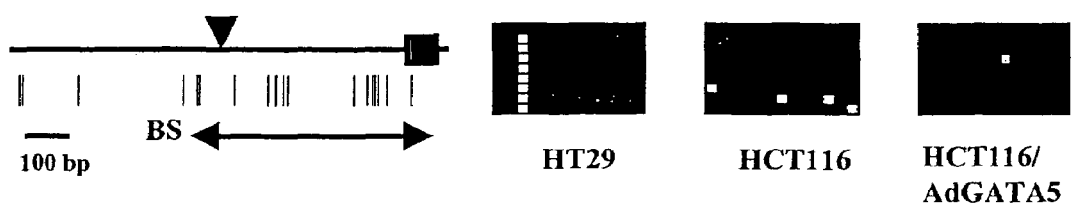

The epigenetic silencing of the TFF genes appeared to be different than for the above described genes. No CpG islands were found between the three TFF genes, which cluster together in order within 45 kb on chromosome 21q22.3, nor between TFF1 and a separate gene located 5 kb upstream (FIG. 5A). The CpG poor promoters of the TFF genes are more typical for those of tissue specific genes, which can normally be differentially methylated in correlation to gene expression status (4). Indeed, for each of the cell lines and normal tissues in which TFF1 was basally silent, only methylated alleles for this gene were detected by MSP, while the promoter was only partially methylated in normal colon and unmethylated in the 3 cell lines where TFF1 was basally expressed (Table 1; FIG. 5B). The promoter regions for TFF2 and TFF3 were examined by bisulfite sequencing. As noted earlier, no promoter region sequences could be amplified for TFF2 in lines RKO and AZ521, where this gene is not basally expressed or reactivated by the demethylating maneuvers. Otherwise, both genes were methylated in cell lines in which the genes were basally expressed or silent (FIGS. 5C and 5D). Thus, TFF2 and TFF3 were the only two downstream genes for which promoter methylation did not correlate with expression status.

GATA-5 Over-Expression Overrides Epigenetic Silencing of Downstream Target Genes The epigenetic profile identified in GI cancers suggests a potentially redundant epigenetic silencing of both upstream transcription factors and genes that have been implicated as potential downstream targets for activation by these factors. To determine whether the changes at the downstream genes were sufficient to prevent their activation by GATA genes, an adenovirus system (16) was used to transiently express exogenous GATA-5 protein in HCT116, RKO and AZ521 cells, in which the GATA-5 gene is basally silent.

Morphological analysis was performed using RKO cells after the GATA-5 construct was overexpressed using an adenovirus system (20). Morphological appearance of the cells was examined by phase contrast microscopy, and GFP expression was examined in the same fields. Immunoblotting of cancer cells was performed using anti-GATA-5 antibody; the 911 cells, which were used to package the viral construct, were used as a positive control for production of the protein. GATA-5 protein was basally undetectable in HCT116 and RKO colon cancer cells, which exhibited GATA-5 promoter methylation. Adenovirus (AdGATA-5) overexpression of GATA-5 resulted in a strong expression of the expected Mr 45,000 form in both the cancer cell lines. The same virus, but expressing the *Escherichia coli* β-galactosidase gene, was used as negative control (Adβgal).

RT-PCR analyses of expression for GATA-5 target genes was performed using RNA extracted from adenovirus-infected cells.

GATA-5 overexpression induced re-expression of each candidate target gene, except TTF3 in all lines, and TFF2 in RKO and AZ521, where the gene was homozygously mutated and/or deleted, in each cell line in which basal expression was absent. Immunoblotting of TFF1 was performed using an anti-TFF1 antibody in culture media, collected after 48 hours, from a positive control gastric cancer cell line MKN45, which has an unmethylated and expressed TFF1 gene, and colon cancer HCT116 cells in which the gene was hypermethylated and silenced. The TFF1 protein was detected in the MKN45 cell media, but was detected in the HCT 116 media only when cells were infected with adeno-GATA-5, but not with Adβgal. The RPMI culture media used for MKN45, and the McCoy's 5A media used for HCT116 cells were used as additional negative controls.

Transient expression of GATA-5 resulted in reactivation, at the transcript level, of inhibin α and TFF1 in all cell lines in which these genes were otherwise basally silent (see Table 1). When examined at the protein level, GATA-5 overexpression resulted in expression of the secreted TFF1 protein (15) in the media of the cell cultures. TFF2 was not activated in RKO and AZ521 cells, in which the promoter is mutated or deleted, as noted previously, but was re-expressed in HCT 116 cells, where the GATA binding sites for this gene are present. Dab2 also was reactivated at the transcript level in the one cell line, HCT116, in which it otherwise was silent. Only one of the downstream genes, TFF3, was not reactivated in the lines in which the gene was basally silenced, suggesting TFF3 may not be a target for GATA-5. In each case in which gene reactivation by GATA-5 occurred, the involved genes remained fully methylated (see, e.g., TFF2—FIG. 5C).

In related studies, hypermethylation of GATA-4 and/or GATA-5 was frequently detected in lung, esophageal, and other cancers.

These results demonstrate that GATA-4 and GATA-5, as well as downstream genes that contain GATA-4 and/or GATA-5 binding sites, are epigenetically silenced by hypermethylation in cancer cells, including colorectal cancer cells and gastric cancer cells. The results further demonstrate that expression of GATA-5 in such cancer cells can override methylation silencing of the target genes.

TABLE 1

Table 1. Summary of methylation status, expression levels of GATA genes and candidate target genes in cancer cells after and before DAC treatment

| | RKO | | | DLD1 | | | HCT116 | | | HT29 | | | LoVo | | |
|---|---|---|---|---|---|---|---|---|---|---|---|---|---|---|---|
| | | Exp[2)] | | | Exp | | | Exp | | | Exp | | | Exp | |
| | Mt[1)] | M | A | Mt | M | A | Mt | M | A | Mt | M | A | Mt | M | A |
| GATA-4 | U | + | + | M | − | + | M | − | + | M | − | + | U/M | + | ++[4)] |
| GATA-5 | M | −[3)] | + | M | − | + | M | − | + | M | − | + | U/M | + | ++ |
| GATA-6 | U | + | + | U | + | + | U | + | + | U | + | + | U | + | + |
| TFF1 | M | − | + | U | + | ++ | M | − | + | U | + | ++ | U | + | ++ |
| TFF2 | NA | − | − | ND | + | + | M | − | + | M | + | + | ND | + | + |
| TFF3 | ND | − | + | ND | + | + | M | − | + | M | + | + | ND | + | ++ |
| Inhibin α | U | + | + | M | − | + | M | − | + | U/M | − | +/− | U/M | + | ++ |
| Dab2 | M | − | + | U | + | + | U | + | + | U | + | + | U | + | + |

TABLE 1-continued

Table 1. Summary of methylation status, expression levels of GATA genes and candidate target genes in cancer cells after and before DAC treatment

|  | SW480 | | | AZ521 | | | Normal colon | | PBL | |
|---|---|---|---|---|---|---|---|---|---|---|
|  | Mt | Exp | | Mt | Exp | | Mt. | Exp | Mt. | Exp |
|  |  | M | A |  | M | A |  |  |  |  |
| GATA-4 | M | − | + | M | − | + | U | + | U | − |
| GATA-5 | M | − | + | M | − | + | U | + | U | − |
| GATA-6 | U | + | + | U | + | + | U | + | U | + |
| TFF1 | M | − | + | M | − | + | U/M | + | M | − |
| TFF2 | ND | + | + | NA | − | − | nd | + | nd | − |
| TFF3 | ND | + | + | ND | − | + | nd | + | nd | − |
| Inhibin α | U | + | ++ | U | + | ++ | U | − | U | − |
| Dab2 | U | + | + | U | + | + | U | + | U | + |

[1] Mt = methylation status; U = unmethylated; M = methylated; NA; genomic sequences were not dected by either MSP and bisulfite sequencing; ND; not done.
[2] Exp = expression; M = mock treatment; A = 5-aza-2'deoxycytidine (DAC) treatment
[3] − = Undetectable level, and + = detectable level of expression, by RT-PCR
[4] ++ = increased expression level from +basal level

TABLE 2

Primer sequences of RT-PCR for GATA1-6 and GATA5 target genes

| Name | Primer S/AS | Sequences | SEQ ID NO: | Sites | Annealing Temp. | PCR Cycles | Size of PCR product (bp) | DMSO |
|---|---|---|---|---|---|---|---|---|
| GATA1 | Sense | TGTGGCGGAGAAATGCCAGTGGG | 10 | C-terminal | 58 C. | 35 | 172 | − |
|  | Antisense | CCTGTGCCTCCCAGACTGGAGC | 11 | exons 4-5 |  |  |  |  |
| GATA2 | Sense | TCTGCAACGCCTGTGGCCTCTAC | 12 | C-terminal | 58 C. | 35 | 251 | − |
|  | Antisense | GATGTGTCCGGAGTGGCTGAAGG | 13 | exons 4-5 |  |  |  |  |
| GATA3 | Sense | CACTCTGGAGGAGGAATGCCAATG | 14 | C-terminal | 60 C. | 35 | 258 | − |
|  | Antisense | AGTGGCTGAAGGGCGAGATGTGG | 15 | exons 4-5 |  |  |  |  |
| GATA4* | Sense | CTGGCCTGTCATCTCACTACG | 16 | C-terminal | 58 C. | 35 | 264 | − |
|  | Antisense | GGTCCGTGCAGGAATTTGAGG | 17 | exons 6-7 |  |  |  |  |
| GATA5* | Sense | TCGCCAGCACTGACAGCTCAG | 18 | C-terminal | 58 or 60 C. | 35 | 290 | +** |
|  | Antisense | TGGTCTGTTCCAGGCTGTTCC | 19 | exons 6-7 |  |  |  |  |
| GATA6* | Sense | TTCTAACTCAGATGATTGCAGC | 20 | C-terminal | 58 C. | 35 | 300 | − |
|  | Antisense | GCTGCACAAAAGCAGACACG | 21 | exons 6-7 |  |  |  |  |
| Dab2 | Sense | CAGTTACCAAATCTACTGACAATGC | 22 | C-terminal | 60 C. | 35 | 241 | − |
|  | Antisense | CAAGGGCAGAAATCAGAACGTGTC | 23 | exons 13-15 |  |  |  |  |
|  | Sense | GCCGCATCCGCTGCGCTGTAGC | 24 | N-terminal | 60 C. | 35 | 240 | − |
|  | Antisense | TGGTGCGGCCTGTTGGTCGGGC | 25 | exons 1-2 |  |  |  |  |
| Inhibin alpha | Sense | ACCTACTGCTCTTCTTGCTGC | 26 | N-terminal | 60 C. | 35 | 337 | − |
|  | Antisense | CGGAACATGTATCTGAAGAGG | 27 | exons 1-2 |  |  |  |  |
| TFF1 | Sense | TGGTCCTGGTGTCCATGCTGG | 28 | exons 2-3 | 58 or 60 C. | 35 | 191 | − |
|  | Antisense | GTCGATGGTATTAGGATAGAAGC | 29 |  |  |  |  |  |
| TFF2 | Sense | GATGCTGTTTCGACTCCAGTGTC | 30 | exons 1-2 | 58 or 60 C. | 35 | 160 | +** |
|  | Antisense | GAGAAGCAGCACTTCCGAGAGG | 31 |  |  |  |  |  |
| TFF3 | Sense | TGGCCTTGCTGTCCTCCAGC | 32 | exons 1-2 | 58 or 60 C. | 35 | 149 | − |
|  | Antisense | CCTGGAGTCAAAGCAGCAGC | 33 |  |  |  |  |  |
| GAPDH* | Sense | GACCACAGTCCATGCCATCAC | 34 |  | 62 C. | 21 | 454 | − |
|  | Antisense | GTCCACCACCCTGTTGCTGTA | 35 |  |  |  |  |  |

*Primer sequences of GATA4/5/6 and GAPDH
**DMSO was added with final conc. 5% in PCR mixture.

TABLE 3

Primer sequences for MSP of GATA4/5/6 and GATA5 target genes

| Name |  | Primer S/AS | Sequences | SEQ ID NO: | Annealing Temp. | PCR Cycles | Size of PCR product (bp) |
|---|---|---|---|---|---|---|---|
| GATA4 | U | Sense | TTTGTATAGTTTTGTAGTTTGTGTTTAGT | 36 | 58 C. | 35 | 142 |
|  |  | Antisense | CCCAACTCACAACTCAAATCCCCA | 37 |  |  |  |
|  | M | Sense | GTATAGTTTCGTAGTTTGCGTTTAGC | 38 | 58 C. | 35 | 136 |
|  |  | Antisense | AACTCGCGACTCGAATCCCCG | 39 |  |  |  |
| GATA5 | U | Sense | TGGAGTTTGTTTTTAGGTTAGTTTTTGGT | 40 | 58 C. | 35 | 147 |
|  |  | Antisense | CAAACCAATACAACTAAACAAACAAACCA | 41 |  |  |  |
|  | M | Sense | AGTTCGTTTTTAGGTTAGTTTTCGGC | 42 | 58 C. | 35 | 140 |
|  |  | Antisense | CCAATACAACTAAACGAACGAACCG | 43 |  |  |  |

TABLE 3-continued

Primer sequences for MSP of GATA4/5/6 and GATA5 target genes

| Name | | Primer S/AS | Sequences | SEQ ID NO: | Annealing Temp. | PCR Cycles | Size of PCR product (bp) |
|---|---|---|---|---|---|---|---|
| GATA6 | U | Sense | GTGTGGGGTAGATTTTGGATTTGT | 44 | 58 C. | 35 | 122 |
| | | Antisense | AAACAACCAAACCTCAAACAAACA | 45 | | | |
| | M | Sense | CGGGGTAGATTTCGGATTCGC | 46 | 58 C. | 35 | 116 |
| | | Antisense | CAACCGAACCTCGAACGAACG | 47 | | | |
| Dab2 | U | Sense | GAATTATATTTTTTGTTGGGAGTGGTTGT | 48 | 60 C. | 35 | 153 |
| | | Antisense | CCAACTAACTATTACCTCCATAAAACA | 49 | | | |
| | M | Sense | TATTTTTCGTCGGGAGTGGTCGC | 50 | 60 C. | 35 | 145 |
| | | Antisense | GACTAACTATTACCTCCGTAAAACG | 51 | | | |
| Inhibin alpha | U | Sense | GGTGGTTAGTAGTAGGTTGTGTTTTGT | 52 | 60 C. | 35 | 162 |
| | | Antisense | CCTATACAAATAATAAATAACACCAAAACC | 53 | | | |
| | M | Sense | GGTTAGTAGTAGGTCGTGTTTCGC | 54 | 60 C. | 35 | 155 |
| | | Antisense | ACGAATAATAAATAACGCCGAAACCG | 55 | | | |
| TFF1 | U | Sense | TAGTGGAGATTATTGTTTTAGAGGATTTTT | 56 | 60 C. | 35 | 121 |
| | | Antisense | TCAAAAATAAAAAACCACCCAAACCCCA | 57 | | | |
| | M | Sense | GTGGAGATTATTGTTTTAGAGGATTTTC | 58 | 60 C. | 35 | 116 |
| | | Antisense | AAAATAAAAAACCGCCCGAACCCCG | 59 | | | |

U: unmethylated, M: methylated

TABLE 4

Primer sequences for Bisulfite Sequencing of GATA4/5/6 and GATA5 target genes.

| Name | Primer S/AS | Sequences | SEQ ID NO: | Annealing Temp. | PCR Cycles | Size of PCR product (bp) |
|---|---|---|---|---|---|---|
| GATA4 | Sense | TAATAAAGTTGATTTTGGGTATTATAG | 60 | 55 | 35 | 389 |
| | Antisense | CCCTACCTACTAAACCTAAAAATTC | 61 | | | |
| GATA5 | Sense | GTTTTAGTTAGTGTATTTAGTTTTAGTTTA | 62 | 55 | 35 | 397 |
| | Antisense | CCACTTAACCCTAACAAACCCTACTC | 63 | | | |
| GATA6 | Sense | GTGAGTTTAATTAGGAGTTTAG | 64 | 53 | 35 | 364 |
| | Antisense | ATATCCCTAAAACCTAAAAACC | 65 | | | |
| TFF1 | Sense | TATTGTAAAAGAATTAGTTTAGGTTTAG | 66 | 58 | 35 | 520 |
| | Antisense | TAACCATTACCTCCTCTCTACTCC | 67 | | | |
| TFF2 | Sense | GTGATTTTGTGTGTGTTTAGTTTTAGATTT | 68 | 58 | 35 | 388 |
| | Antisense | CCCTCCAAAACACATAACCCCAAAAC | 69 | | | |
| TFF3 | Sense | GTAGGGTTTTGATTTATTTAGAGTTGTTTG | 70 | 58 | 35 | 528 |
| | Antisense | AACCAAAACCAACCCCAACATACAAAAC | 71 | | | |

REFERENCES CITED

Each of the following articles is incorporated herein by reference.

1. Al-azzeh et al., 2000. Transcription factor GATA-6 activates expression of gastroprotective trefoil genes TFF1 and TFF2. Biochim Biophys Acta 1490:324-32.
2. Azarschab et al., 2001. Aspirin promotes TFF2 gene activation in human gastric cancer cell lines. FEBS Lett 488:206-10.
3. Bai et al., 2000. Distinct expression of CDX2 and GATA4/5, development-related genes, in human gastric cancer cell lines. Mol Carcinog 28:184-8.
4. Bird, A. 2002. DNA methylation patterns and epigenetic memory. Genes Dev 16:6-21.
5. Boudreau et al., 2002. Hepatocyte nuclear factor-1 alpha, GATA-4, and caudal related homeodomain protein Cdx2 interact functionally to modulate intestinal gene transcription. Implication for the developmental regulation of the sucraseisomaltase gene. J Biol Chem 277:31909-17.
6. Cameron et al., 1999. Synergy of demethylation and histone deacetylase inhibition in the re-expression of genes silenced in cancer. Nat Genet. 21:103-7.
7. Cameron et al., 1999. p15(INK4B) CpG island methylation in primary acute leukemia is heterogeneous and suggests density as a critical factor for transcriptional silencing. Blood 94:2445-51.
8. Esteller et al., 2001. A gene hypemethylation profile of human cancer. Cancer Res 61:3225-9.
9. Farrell et al., 2002. TFF2/SP-deficient mice show decreased gastric proliferation, increased acid secretion, and increased susceptibility to NSAID injury. J Clin Invest 109:193-204.
10. Feng et al., 1998. Testicular GATA-1 factor up-regulates the promoter activity of rat inhibin alpha-subunit gene in MA-10 Leydig tumor cells. Mol Endocrinol 12:378-90.
11. Fujikura et al., 2002. Differentiation of embryonic stem cells is induced by GATA factors. Genes Dev 16:784-9.
12. Fujimoto et al., 2000. DNA hypermethylation at the pS2 promoter region is associated with early stage of stomach carcinogenesis. Cancer Lett 149:125-34.
13. Fujiwara et al., 1993. Evidence for the presence of two tumor suppressor genes on chromosome 8p for colorectal carcinoma. Cancer Res 53:1172-4.
14. Gao et al., 1998. Distinct functions are implicated for the GATA-4, -5, and -6 transcription factors in the regulation of intestine epithelial cell differentiation. Mol Cell Biol 18:2901-11.
15. Gouyer et al., 2001. Specific secretion of gel-forming mucins and TFF peptides in HT-29 cells of mucin-secreting phenotype. Biochim Biophys Acta 1539:71-84.

16. He et al., 1998. A simplified system for generating recombinant adenoviruses. Proc Natl Acad Sci USA 95:2509-14.
17. Herman et al., 1996. Methylation-specific PCR: a novel PCR assay for methylation status of CpG islands. Proc Natl Acad Sci USA 93:9821-6.
18. Jones et al., 1997. Frequent loss of heterozygosity on chromosome arm 18q in squamous cell carcinomas. Identification of 2 regions of loss—18q11.1-q12.3 and 18q21.1-q23. Arch Otolaryngol Head Neck Surg 123: 610-4.
19. Jones and Baylin. 2002. The fundamental role of epigenetic events in cancer. Nat Rev Genet. 3:415-28.
20. Kamitani et al., 2000. A GATA binding site is involved in the regulation of 15-lipoxygenase-1 expression in human colorectal carcinoma cell line, caco-2. FEBS Lett 467:341-7.
21. Ketola et al., 1999. Expression and regulation of transcription factors GATA-4 and GATA-6 in developing mouse testis. Endocrinology 140:1470-80.
22. Kuo et al., 1997. GATA4 transcription factor is required for ventral morphogenesis and heart tube formation. Genes Dev 11: 1048-60.
23. Lassus et al., 2001. Comparison of serous and mucinous ovarian carcinomas: distinct pattern of allelic loss at distal 8p and expression of transcription factor GATA-4. Lab Invest 81:517-26.
24. Laverriere et al., 1994. GATA-4/5/6, a subfamily of three transcription factors transcribed in developing heart and gut. J Biol Chem 269:23177-84.
25. Lefebvre et al., 1996. Gastric mucosa abnormalities and tumorigenesis in mice lacking the pS2 trefoil protein. Science 274:259-62.
26. Leonard et al., 1993. Dynamics of GATA transcription factor expression during erythroid differentiation. Blood 82:1071-9.
27. Matzuk et al., 1992. Alpha-inhibin is a tumour-suppressor gene with gonadal specificity in mice. Nature 360: 313-9.
28. Molkentin, J. D. 2000. The zinc finger-containing transcription factors GATA-4, -5, and -6. Ubiquitously expressed regulators of tissue-specific gene expression. J Biol Chem 275:38949-52.
29. Molkentin et al., 1997. Requirement of the transcription factor GATA4 for heart tube formation and ventral morphogenesis. Genes Dev 11:1061-72.
30. Morrisey, E. E. 2000. GATA-6: the proliferation stops here: cell proliferation in glomerular mesangial and vascular smooth muscle cells. Circ Res 87:638-40.
31. Morrisey et al., 1998. GATA6 regulates HNF4 and is required for differentiation of visceral endoderm in the mouse embryo. Genes Dev 12:3579-90.
32. Nemer et al., 1999. Functional analysis and chromosomal mapping of Gata5, a gene encoding a zinc finger DNA-binding protein. Mamm Genome 10:993-9.
33. Park et al., 2000. Somatic mutations of the trefoil factor family 1 gene in gastric cancer. Gastroenterology 119: 691-8.
34. Rhee et al., 2002. DNMT1 and DNMT3b cooperate to silence genes in human cancer cells. Nature 416:552-6.
35. Rhee et al., 2000. CpG methylation is maintained in human cancer cells lacking DNMT1. Nature 404:1003-7.
36. Schmitt et al., 2002. Hypermethylation of the inhibin alpha-subunit gene in prostate carcinoma. Mol Endocrinol 16:213-20.
37. Sheng et al., 2001. Chromosomal location of murine disabled-2 gene and structural comparison with its human ortholog. Gene 268:31-9.
38. Sheng et al., 2000. Restoration of positioning control following Disabled-2 expression in ovarian and breast tumor cells. Oncogene 19:4847-54.
39. Simon, M. C. 1995. Gotta have GATA. Nat Genet. 11:9-11.
40. Singh et al., 1998. Expression of oestrogen receptor and oestrogen-inducible genes pS2 and ERD5 in large bowel mucosa and cancer. J Pathol 184:153-60.
41. Suzuki et al., 2002. A genomic screen for genes upregulated by demethylation and histone deacetylase inhibition in human colorectal cancer. Nat Genet 31:141-9.
42. van Wering et al., 2002. Physical interaction between GATA-5 and hepatocyte nuclear factor-1 alpha results in synergistic activation of the human lactase-phlorizin hydrolase promoter. J Biol Chem 277:27659-67.
43. Widschwendter and Jones. 2002. DNA methylation and breast carcinogenesis. Oncogene 21:5462-82.
44. Wright et al., 1997. Rolling in the clover: trefoil factor family (TFF)-domain peptides, cell migration and cancer. FEBS Lett 408:121-3.

Although the invention has been described with reference to the above example, it will be understood that modifications and variations are encompassed within the spirit and scope of the invention. Accordingly, the invention is limited only by the following claims.

What is claimed is:

1. A method of detecting lung or esophageal cancer cells in a sample, comprising: contacting a 5' promoter region of an endogenous nucleic acid molecule encoding GATA-4 from a control lung or esophageal cell sample and a suspected lung or esophageal cancer cell sample with a chemical reagent that selectively modifies an unmethylated cytosine residue in a CpG dinucleotide of the nucleic acid, wherein the reagent produces a modified nucleic acid template comprising a uracil-containing GATA-4 promoter, and detecting a non-uracil containing GATA-4 promoter template and a template comprising a uracil-containing GATA-4 promoter in the control cell or cancer cell sample, wherein detection of a non-uracil containing GATA-4 promoter template in the cancer cell sample is indicative of epigenetic silencing, and wherein the detection of the epigenetically silenced GATA-4 promoter indicates that the sample comprises lung or esophageal cancer cells therein.

2. The method of claim 1, wherein the chemical reagent comprises bisulfite ions, wherein unmethylated cytosine residues in the 5' promoter region of the nucleic acid are converted to bisulfite modified cytosine residues,
said method further comprising exposing the bisulfite ion treated nucleic acid to alkaline conditions, whereby bisulfite modified cytosine residues are converted to uracil residues, and
detecting an amount or distribution of uracil residues in the 5' promoter region of the bisulfite ion treated nucleic acid in the sample,
wherein a decrease in the amount or distribution of uracil residues in the 5' promoter region of nucleic acid in the sample, as compared to the amount or distribution of uracil residues in a corresponding bisulfite ion treated unmethylated nucleic acid following exposure to alkaline conditions, is indicative of methylation of cytosine residues in CpG dinucleotides in the 5' promoter region of the nucleic acid, thereby detecting methylation silencing of the nucleic acid in the sample.

3. The method of claim 2, wherein detecting the amount or distribution of uracil residues comprises determining the nucleotide sequence of the bisulfite modified 5' promoter region of the nucleic acid the following exposure to alkaline conditions.

4. The method of claim 3, wherein detecting the amount or distribution of uracil residues comprises contacting the bisulfite ion treated nucleic acid sequence, following exposure to alkaline conditions, with an oligonucleotide that selectively hybridizes to the 5' promoter region of the nucleic acid containing uracil residues, and
detecting selective hybridization of the oligonucleotide.

5. The method of claim 4, wherein the oligonucleotide is a substrate for a primer extension reaction, and wherein detecting selective hybridization comprises detecting a product of the primer extension reaction.

6. The method of claim 2, wherein detecting the amount or distribution of uracil residues comprises
contacting the 5' promoter region of the nucleic acid with an amplification primer pair comprising a forward primer and a reverse primer under conditions suitable for amplification, wherein at least one primer of the primer pair comprises an oligonucleotide that selectively hybridizes to a nucleotide sequence of the 5' promoter region containing uracil residues,
wherein generation of an amplification product is indicative of methylation of cytosine residues in CpG dinucleotides in the 5' promoter region of the nucleic acid, thereby detecting methylation silencing of the nucleic acid in the sample.

7. The method of claim 6, wherein the amplification primer pair comprises a primer pair as set forth in SEQ ID NOS:38 and 39.

8. The method of claim 2, wherein detecting the amount or distribution of uracil residues comprises
contacting the 5' promoter region of the nucleic acid with an amplification primer pair comprising a forward primer and a reverse primer under conditions suitable for amplification, wherein both primers of the primer pair selectively hybridize to a nucleotide sequence of the 5' promoter region containing cytosine residues, but not to a corresponding nucleotide sequence of the 5' promoter region containing uracil residues, and
whereby generation of an amplification product is indicative of a lack of methylation of cytosine residues in CpG dinucleotides in the 5' regulatory region of the nucleic acid, thereby detecting methylation silencing of the nucleic acid in the sample.

9. The method of claim 8, wherein the amplification primer pair comprises a primer pair as set forth in SEQ ID NOS: 36 and 37.

10. The method of claim 2, wherein detecting the amount or distribution of uracil residues comprises:
contacting in the 5' promoter region of the nucleic acid with a first amplification primer pair and a second amplification primer pair under conditions suitable for amplification,
wherein the first amplification primer pair comprises a forward primer and a reverse primer, wherein at least one primer of the first primer pair comprises an oligonucleotide that selectively hybridizes to a nucleotide sequence of the 5' promoter region of the gene containing uracil residues, and
wherein the second amplification primer pair comprises a forward primer and a reverse primer, wherein both primers of the second primer pair selectively hybridize to a nucleotide sequence of the 5' promoter region of the nucleic acid containing cytosine residues, but not to a corresponding nucleotide sequence of the 5' promoter region of the nucleic acid containing uracil residues, and
wherein an amplification product, if any, generated by the first primer pair has a first length, and wherein an amplification product, if any, generated by the second primer pair has a second length, which is different from the first length, wherein the difference between the first and second length of the amplification products is indicative of uracil residues and, therefore, methylation of cytosine residues in CpG dinucleotides in the 5' promoter region of the nucleic acid, thereby detecting methylation silencing of the nucleic acid in the sample.

11. The method of claim 1, which is performed in a high throughput format, wherein the sample, or extract of the sample, comprises one of a plurality of samples, or extracts of the samples, or a combination thereof.

12. The method of claim 1, wherein the sample comprises a sample cell obtained from a subject.

13. The method of claim 12, wherein the subject is a human subject.

14. The method of claim 12, wherein the sample comprises a biological fluid.

15. A method of detecting a lung or esophageal cancer cell in a sample, comprising: i) contacting a 5' promoter region of an endogenous nucleic acid molecule encoding an epigenetically silenced GATA-4 from a sample lung or esophageal cancer cell with a first chemical reagent that selectively modifies an unmethylated cytosine residue in a CpG dinucleotide of the nucleic acid, wherein the first reagent produces a modified nucleic acid template comprising a uracil-containing gene promoter; ii) detecting the presence or absence of a uracil containing product due to the contacting of step (i); iii) contacting the endogenous nucleic acid molecule from the sample lung or esophageal cancer cell with a second chemical agent, wherein the second chemical agent demethylates cytosine residues in a CpG dinucleotide; and iv) determining the presence or absence of a transcript from the endogenous nucleic acid molecule encoding the silenced GATA-4 subsequent to the contacting of step (iii), wherein the absence of detection of a product in step (ii) and detecting the presence of the transcript of step (iv) correlates with the reactivation of expression from the silenced gene, wherein the epigenetic silencing is methylation silencing, and wherein the detection of the epigenetically silenced nucleic acid indicates the presence of a lung or esophageal cancer cell in the sample.

16. The method of any of claims 1 or 15, wherein the sample is an organ sample, a tissue sample, a biological fluid sample or a cell sample.

17. A method of detecting lung or esophageal cancer cells in a sample, comprising: contacting a 5' promoter region of an endogenous nucleic acid molecule encoding GATA-4 from a control lung or esophageal cell and a sample lung or esophageal cancer cell with a first chemical reagent that selectively modifies an unmethylated cytosine residue in a CpG dinucleotide of the nucleic acid and a second reagent which cleaves the modified dinucleotide, wherein the combined reagents produce fragments of the 5' promoter of the endogenous nucleic acid encoding GATA-4, and comparing patterns of separated fragments between the control and sample cells, wherein detection of gaps between the control sample fragments is indicative of an epigenetically silenced GATA-4 promoter, which indicates that the sample comprises lung or esophageal cancer cells therein.

18. The method of claim 17, wherein the first reagent is hydrazine.

19. The method of claim 17, wherein the second reagent is piperidine.

* * * * *

SEQUENCE LISTING

```
<160> NUMBER OF SEQ ID NOS: 71

<210> SEQ ID NO 1
<211> LENGTH: 3372
<212> TYPE: DNA
<213> ORGANISM: Homo sapiens

<400> SEQUENCE: 1
gtcgccgctg cagctccggg ggctcccagg ggagcgtgcg cggaacctcc aggcccagca      60
ggaccccggc tgcggcgagg aggaaggagc cagcctagca gcttctgcgc ctgtggccgc     120
gggtgtcctg gaggcctctc ggtgtgacga gtgggggacc cgaaggctcg tgcgccacct    180
```

-continued

| | | | | |
|---|---|---|---|---|
| ccaggcctgg | acgctgccct | ccgtcttctg | cccccaatag | gtgcgccgga ccttcaggcc | 240 |
| ctggggtgaa | ttcagctgct | cctacatcag | cttccggaac | accaaaaat tcaaattggg | 300 |
| atttccgga | gtaaacaaga | gcctagagcc | ctttgctcaa | tgctggattt aatacgtata | 360 |
| tatttttaag | cgagttggtt | ttttccccctt | tgattttga | tcttcgcgac agttcctccc | 420 |
| acgcatatta | tcgttgttgc | cgtcgttttc | tctccccgcg | tggctccttg acctgcgagg | 480 |
| gagagagagg | acaccgaagc | cgggagctcg | caggaccat | gtatcagagc ttggccatgg | 540 |
| ccgccaacca | cgggccgccc | cccggtgcct | acgaggcggg | cggccccggc gccttcatgc | 600 |
| acggcgcggg | cgccgcgtcc | tcgccagtct | acgtgcccac | accgcgggtg ccctcctccg | 660 |
| tgctgggcct | gtcctacctc | cagggcggag | gcgcgggctc | tgcgtccgga ggcgcctcgg | 720 |
| gcggcagctc | cggtggggcc | gcgtctggtg | cggggcccgg | gacccagcag ggcagcccgg | 780 |
| gatggagcca | ggcgggagcc | gacggagccg | cttacacccc | gccgccggtg tcgccgcgct | 840 |
| tctccttccc | ggggaccacc | gggtccctgg | cggccgccgc | cgccgctgcc gcggcccggg | 900 |
| aagctgcggc | ctacagcagt | ggcggcgag | cggcgggtgc | gggcctggcg ggccgcgagc | 960 |
| agtacgggcg | cgccggcttc | gcgggctcct | actccagccc | ctaccggct tacatggccg | 1020 |
| acgtgggcgc | gtcctgggcc | gcagccgccg | ccgcctccgc | cggccccttc gacagcccgg | 1080 |
| tcctgcacag | cctgcccggc | cgggccaacc | cggccgcccg | acaccccaat ctcgatatgt | 1140 |
| ttgacgactt | ctcagaaggc | agagagtgtg | tcaactgtgg | ggctatgtcc accccgctct | 1200 |
| ggaggcgaga | tgggacgggt | cactatctgt | gcaacgcctg | cggcctctac acaagatga | 1260 |
| acggcatcaa | ccggccgctc | atcaagcctc | agcgccggct | gtccgcctcc cgccgagtgg | 1320 |
| gcctctcctg | tgccaactgc | cagaccacca | ccaccacgct | gtggcgccgc aatgcggagg | 1380 |
| gcgagcctgt | gtgcaatgcc | tgcggcctct | acatgaagct | ccacggggta cccaggcctc | 1440 |
| ttgcaatgcg | gaaagagggg | atccaaacca | gaaaacggaa | gcccaagaac ctgaataaat | 1500 |
| ctaagacacc | agcagctcct | tcaggcagtg | agagccttcc | tcccgccagc ggtgcttcca | 1560 |
| gcaactccag | caacgccacc | accagcagca | gcgaggagat | gcgtcccatc aagacggagc | 1620 |
| ctggcctgtc | atctcactac | gggcacagca | gctccgtgtc | ccagacgttc tcagtcagtg | 1680 |
| cgatgtctgg | ccatgggccc | tccatccacc | ctgtcctctc | ggccctgaag ctctccccac | 1740 |
| aaggctatgc | gtctcccgtc | agccagtctc | cacagaccag | ctccaagcag gactcttgga | 1800 |
| acagcctggt | cttggccgac | agtcacgggg | acataatcac | tgcgtaatct tccctcttcc | 1860 |
| ctcctcaaat | tcctgcacgg | acctgggact | tggaggatag | caaagaagga ggccctgggc | 1920 |
| tcccagggc | cggcctcctc | tgcctggtaa | tgactccaga | acaacaactg ggaagaaact | 1980 |
| tgaagtcgac | aatctggtta | ggggaagcgg | gtgttggatt | ttctcagatg cctttacacg | 2040 |
| ctgatgggac | tggagggagc | caccccttca | gcacgagcac | actgcatctc tcctgtgagt | 2100 |
| tggagacttc | tttcccaaga | tgtccttgtc | ccctgcgttc | cccactgtgg cctagaccgt | 2160 |
| gggttttgca | ttgtgtttct | agcaccgagg | atctgagaac | aagcggaggg ccgggccctg | 2220 |
| ggaccctgc | tccagcccga | atgacggcat | ctgtttgcca | tgtacctgga tgcgacgggc | 2280 |
| ccctggggac | aggcccttgc | ccatccatc | cgcttgaggc | atggcaccgc cctgcatccc | 2340 |
| taataccaaa | tctgactcca | aaattgtggg | gtgtgacata | caagtgactg aacacttcct | 2400 |
| ggggagctac | aggggcactt | aacccaccac | agcacagcct | catcaaaatg cagctggcaa | 2460 |
| cttctccccc | aggtgccttc | cccctgctgc | cggcctttgc | tccttcactt ccaacatctc | 2520 |

-continued

| | |
|---|---|
| tcaaaataaa aatccctctt cccgctctga gcgattcagc tctgcccgca gcttgtacat | 2580 |
| gtctctcccc tggcaaaaca agagctgggt agtttagcca aacggcaccc cctcgagttc | 2640 |
| actgcagacc cttcgttcac cgtgtcacac atagagcggt tctgagtaag aacaaaacgt | 2700 |
| tctgctgctc aagccagtct ggcaagcact cagcccagcc tcgaggtcct tctggggaga | 2760 |
| gtgtaagtgg acagagtcct ggtcaggggg caggagtgtc ccaagggctg ccccacctgc | 2820 |
| tgtctgtctg ctcctcctag cccttggtca gatggcagcc agagtccctc aggacctgca | 2880 |
| gcctcgcccc ggcagaagtc ttttgtccag gaggcaaaaa gccagagatt ctgcaacacg | 2940 |
| aattcgaagc aaacaaacac aacacaacag aattcctgga agaagacga ctgctaagac | 3000 |
| acggcagggg ggcctggagg gagcctccga ctctgagctg ctccgggatc tgccgcgttc | 3060 |
| tcctctgcac attgctgttt ctgcccctga tgctggagct caaggagact ccttcctctt | 3120 |
| tctcagcaga gctgtagctg actgtggcat tactacgcct ccccacacgc ccagacccct | 3180 |
| cactccaaaa tcctactggc tgtagcgagg aatacctttg aaccaagatt ctgttttaat | 3240 |
| catcatttac attgttttct tccaaaggcc ccctcgtata ccctccctaa cccacaaacc | 3300 |
| tgttaacatt gtcttaaggt gaaatggctg gaaaatcagt atttaactaa taaatttatc | 3360 |
| tgtattcctc tt | 3372 |

```
<210> SEQ ID NO 2
<211> LENGTH: 2630
<212> TYPE: DNA
<213> ORGANISM: Homo sapiens

<400> SEQUENCE: 2
```

| | |
|---|---|
| ccaccgccac cgccgtgccc tgccgccctc cctgcccgct ggtcaagacc acgcctggga | 60 |
| ggatgtacca gagcctggcg ctggccgcga gccccgcca ggccgcctac gccgactcgg | 120 |
| gctccttcct gcacgctccg ggcgccggct ctccgatgtt tgtgccgccg gcgcgcgtcc | 180 |
| cctcgatgct gtcctacctg tccgggtgtg agccgagccc gcagcccccc gagctcgctg | 240 |
| cgcgccccgg ctgggcgcag acagccaccg cggattcgtc ggccttcggc ccgggcagtc | 300 |
| cgcacccccc agccgcgcac ccgcccgggg ccaccgcctt ccctttcgcg cacagcccct | 360 |
| cggggcccgg cagcggcggc agcgcggggg gccgagacgg cagtgcctac cagggcgcgc | 420 |
| tgttgcctcg agaacagttc gcggccccgc ttgggcggcc ggtggggacc tcgtactccg | 480 |
| ccacctaccc ggcctacgtg agccccgacg tggcccagtc ctggactgcc gggcccttcg | 540 |
| atggcagcgt cctgcacggc ctcccaggcc gcaggcccac cttcgtgtcc gacttcttgg | 600 |
| aggagttccc gggtgagggt cgtgagtgtg tcaactgcgg ggccctgtcc acaccgctgt | 660 |
| ggcgccgaga cggcaccggc cactacctgt gcaatgcctg cggcctctac cacaagatga | 720 |
| atggcgtcaa ccggccgctc gttcggcctc agaagcgcct gtcctcgtcc cgccgcgccg | 780 |
| gcctctgctg caccaactgc cacacgacca acaccacgcg tgtggcggcgg aactcggagg | 840 |
| gggagcccgt gtgcaatgcc tgcggcctct acatgaagct gcacggggtg ccgcggcctc | 900 |
| tggctatgaa gaaagaaagc atccagacac ggaagcggaa gccaaagacc atcgccaagg | 960 |
| ccaggggctc ctcaggatcc acaaggaatg cctcggcctc cccatctgct gtcgccagca | 1020 |
| ctgacagctc agcagccact tcgaaagcca agcccagcct ggcgtcccca gtgtgccctg | 1080 |
| ggcccagcat ggccccccag gcctctggcc aggaggatga ctctcttgcc cccggccact | 1140 |
| tggagttcaa gttcgagcct gaggactttg ccttcccctc cacggcccca agcccccagg | 1200 |
| ctggcctcag gggggctctg cgccaagagg cctggtgtgc gctggccttg gcctaggtcc | 1260 |

```
ccaggccagc ccatgtcagg ggaacagcct ggaacagacc acccactgag tcacctccgt    1320
gcctgctttg ctccagcaca gcagagacca gcaggccccc aacccagag actgggtctg     1380 ctggagtctc cacacagtgg tggggaggcc ttctggacag acggcagtcg ggccccagag    1440
caagaaggct ggtgagggaa gggctcagct tcccacccca cgtacagcaa gggactcccc    1500
aggtgcggcc caaggctccg gaccacactg gcccctgcg gcgaggcca acgcagggca      1560 ccaccaccac caacttgaat tccgtcatca atgctcaccg tcaatatgtt tacaagttgt    1620
agcagttggg ggaaaacagt caacctccca gtgtaaaacc aagattccca gtgaagcacc    1680
tgaggccaag caggggagag gaatgagggg agcagctgga catgggcctc ctgaggcctc    1740
ggggctgtcc ttcattgccc acatggatag acggagctgt ggtgcagaga acttttcccg    1800
caacaggtgc aggactgcca gggatcggag tgcgggccgc gcacggtgcc aggattccgc    1860
cgaggggaag ccgctcacat tgcagtcatc acagacttac gcacttgttt ggacagtttt    1920
tccagagggg atgggaaagg gccttgttct agctgaatct gtgtatcatg accatttctg    1980
acaggcagaa tgaattgtct ggtagccctg tcctgaccca tccaagcgct gttggggctg    2040
gtggtgacgt ggtcacatgt cctggcatat ctggggccac gcagtttagt ctcttgtccc    2100
aggagaattg ttagtgaccc ctcttttctct tgcaagcccc ctccacactg ggttggatga    2160
taccttaatg agtgacgctg gcgagaggca ccctacccga cgcagctgtg aatggccggt    2220
gatgtatgtc aggaggccac agggagcgga ggagcggggc aggcagccac aggggccctg    2280
cggggagcac atcctcgcct ccgtccggct gctgcccttc aacaacaagc cctgattttt    2340
ccagcaatgc cagaaacctg gatttaagt cttccaattt gattcaaaaa tatttttaac     2400
attgtgagcc agctagaccc ccagtgcacc accccatatt gaaaacagt tgtctggcat     2460 cagcttcagg agcgggtccg gtcattctga aactgtccct ccagaggttc ttccagcccc    2520
acttctatgc gatgtcatct tttctaaaag agacaaatga agccacaggg aaagtgaaat    2580
aaagccttga acctcaaaaa aaaaaaaaa aaaaaaaaa aaaaaaaaa                  2630
```

<210> SEQ ID NO 3
<211> LENGTH: 508
<212> TYPE: DNA
<213> ORGANISM: Homo sapiens

<400> SEQUENCE: 3

```
atccctgact cggggtcgcc tttggagcag agaggaggca atggccacca tggagaacaa      60
ggtgatctgc gccctggtcc tggtgtccat gctggccctc ggcaccctgg ccgaggccca    120
gacagagacg tgtacagtgg ccccccgtga agacagaat tgtggttttc ctggtgtcac     180
gccctcccag tgtgcaaata agggctgctg tttcgacgac accgttcgtg gggtcccctg    240
gtgcttctat cctaatacca tcgacgtccc tccagaagag gagtgtgaat tttagacact    300
tctgcaggga tctgcctgca tcctgacgcg gtgccgtccc cagcacggtg attagtccca    360
gagctcggct gccaccttca ccggacacct cagacacgct tctgcagctg tgcctcggct    420
cacaacacag attgactgct ctgactttga ctactcaaaa ttggcctaaa aattaaaga     480 gatcgatatt aaaaaaaaaa aaaaaaaa                                       508
```

<210> SEQ ID NO 4
<211> LENGTH: 616
<212> TYPE: DNA
<213> ORGANISM: Homo sapiens

```
<400> SEQUENCE: 4
atgcattctg caagccaccc tggggtgcag ctgagctaga catgggacgg cgagacgccc        60
agctcctggc agcgctcctc gtcctggggc tatgtgccct ggcggggagt gagaaaccct       120 cccctgcca gtgctccagg ctgagcccc ataacaggac gaactgcggc ttccctggaa         180
tcaccagtga ccagtgtttt gacaatggat gctgtttcga ctccagtgtc actggggtcc      240
cctggtgttt ccaccccctc ccaaagcaag agtcggatca gtgcgtcatg gaggtctcag      300
accgaagaaa ctgtggctac ccgggcatca gccccgagga atgcgcctct cggaagtgct     360
gcttctccaa cttcatcttt gaagtgccct ggtgcttctt cccgaagtct gtggaagact     420
gccattacta agagaggctg gttccagagg atgcatctgg ctcaccgggt gttccgaaac     480
caaagaagaa acttcgcctt atcagcttca tacttcatga atcctgggt tttcttaacc        540 atctttttcct cattttcaat ggtttaacat ataatttctt taaataaaac ccttaaaatc      600
tgctaaaaaa aaaaaa                                                        616

<210> SEQ ID NO 5
<211> LENGTH: 685
<212> TYPE: DNA
<213> ORGANISM: Homo sapiens

<400> SEQUENCE: 5
gccaaaacag tgggggctga actgaccctct cccctttggg agagaaaaac tgtctgggag      60
cttgacaaag gcatgcagga gagaacagga gcagccacag ccaggaggga gagccttccc     120
caagcaaaca atccagagca gctgtgcaaa aacggtgca taaatgaggc ctcctggacc       180
atgaagcgag tcctgagctg cgtcccggag cccacggtgg tcatggctgc cagagcgctc     240
tgcatgctgg ggctggtcct ggccttgctg tcctccagct ctgctgagga gtacgtgggc     300
ctgtctgcaa accagtgtgc cgtgccagcc aaggacaggg tggactgcgg ctaccccat      360 gtcacccca aggagtgcaa caaccggggc tgctgctttg actccaggat ccctggagtg     420
ccttggtgtt tcaagcccct gcaggaagca gaatgcacct tctgaggcac ctccagctgc     480
ccccggccgg gggatgcgag gctcggagca cccttgcccg gctgtgattg ctgccaggca     540
ctgttcatct cagcttttct gtcccttgtc tcccggcaag cgcttctgct gaaagttcat     600
atctggagcc tgatgtctta acgaataaag gtcccatgct ccacccgagg acagttcttc     660
gtgcctgaaa aaaaaaaaaaa aaaaa                                             685

<210> SEQ ID NO 6
<211> LENGTH: 3268
<212> TYPE: DNA
<213> ORGANISM: Homo sapiens

<400> SEQUENCE: 6
gccggggaag tcatgctcgc ttcacggagg caatagctag ccggtgtctg tgggaggtta        60 tgtttattg agacttctcc atcgggatcg cctggtgtca ccaagtgtcc actggtactg       120
aggtttgctg cctgccttct tgccatgtct aacgaagtag aaacaagtgc aaccaatggt      180
cagcccgacc aacaggccgc accaaaagca ccctcaaaga aggaaaaaaa gaaaggccct     240
gaaaagacag atgaatatct cctagcaagg ttcaaaggcg atggcgtaaa atataaggcc      300
aagctgattg gcattgatga tgtgccagat gcaagagggg ataaaatgag ccaagactct      360
atgatgaaac taagggggaat ggcggcacgt ggtcggtctc aggacaacaa caaacaaagg      420
atctgggtca acatttccct ttctgggata aaaataattg atgagaaaac tgggggtaata      480
```

-continued

```
gagcatgaac atccagtaaa taagatttct ttcattgccc gtgatgtgac agacaaccgg    540
gcatttggtt acgtgtgtgg aggagaaggc cagcatcagt ttttttaccat aaaaaccggg   600
caacaggctg aaccattagt tgttgatctt aaagaccttt ttcaagttat ctataatgta    660
aagaaaaagg aagaagaaaa gaaaaagata gaggaagcca gcaaagcagt tgagaatggg    720
agtgaggccc taaggattct agatgaccaa actaacaaac tgaaatcggg tgttgaccag    780
atggatttgt ttggggacat gtctacacct cctgacctaa atagtccaac agaaagcaaa    840
gatatcctgt tagtggatct aaactctgaa atcgacacca atcagaattc tttaagagaa    900
aatccattct taacaaacgg catcacctcc tgttctcttc ctcgaccaac gcctcaggca    960
tccttcttgc ctgaaaatgc ctttttctgcc aatctcaact tctttcccac ccctaatcct   1020
gatcctttcc gtgacgatcc tttcacacag ccagaccaat cgacaccttc ttcgtttgat   1080
tctctcaaat ctccagatca gaagaaagag aattcgagta gctcgtctac tccgctgagt   1140
aatgggcccc tgaatggtga tgttgactac tttggtcagc aatttgacca gatctctaac   1200
cggactggca acaggaagc tcaggcaggc ccatggccct tttcaagttc gcaaacccag    1260
ccagcagtga gaactcaaaa tggggtatct gaaagagaac agaacggctt ctctgtcaaa   1320
tcctccccga acccttttgt gggaagccct cccaaaggac tgtccataca gaatggcgta   1380
aagcaggact tggaaagctc tgtccagtcc tcaccacatg actccatagc cattatccca   1440
cctccacaaa gtaccaaacc aggaagaggc agaaggactg ctaagtcttc agccaatgac   1500
ttgcttgcat cagacatctt tgctcctccc gtctcagaac cttcaggcca ggcgtcaccc   1560
acaggacaac ctacagccct gcagcccaac cctctggatc tcttcaaaac aagtgctcct   1620
gccccagtgg ggcccctggt gggtctaggt ggtgtaactg tcacactccc tcaggcagga   1680
ccatggaaca cagcatcttt ggtcttcaat cagtcccctt caatggctcc gggagccatg   1740
atgggtggtc aaccttcagg ttttagtcag cccgtcattt ttggtacaag tccagctgtt   1800
tcaggttgga accagccttc accctttgca gcctcaactc cccctccagt gcctgttgtc   1860
tggggcccctt ctgcatctgt ggcacccaat gcttggtcaa caacaagccc tttggggaat   1920
ccttttcaga gcaatatttt tccagctcct gctgtgtcca ctcagccccc atccatgcac   1980
tcctctctcc tggtcactcc tcctcagcca cctcccagag ctggccctcc caaggacatc   2040
tccagtgatg ccttcactgc cttagaccca cttggggata aagagatcaa ggatgtgaaa   2100
gaaatgttta aggatttcca actgcggcag ccacctgctg tgcccgcgcg aagggagag    2160
cagacttctt ctgggacttt gagtgccttt gccagttatt tcaacagcaa ggttggcatt   2220
cctcaggaga atgcagacca tgatgacttt gatgctaatc aactattgaa caagatcaat   2280
gaaccaccaa agccagctcc cagacaagtt tccctgccag ttaccaaatc tactgacaat   2340
gcatttgaga accctttctt taaagattct tttggttcat cacaagcctc tgtggcttct   2400
tctcaacctg tatcttctga gatgtatagg gatccatttg gaaatccttt tgcctaaatt   2460
ctgaacttgg tctgcagacc atccagagga ataaaaaggt tggccttagt agtcaaaaac   2520
aaagctgata gccagacacg ttctgatttc tgccttgtt ccagctttga cgtattatct   2580
gttgccttat ttctcattgc ctcttctact tgtaaaatgc ttttcacttt ctgtctaggt   2640
taaagctaaa ctgaatctat ggctttaaat aaattaagat cctaaactct ctagcttaag   2700
tgtaaatgaa gtacagtagt ttccctactg aaccctacct cttgtgtccc tggaaccttc   2760
tagaacacct gccttctacc ctctggttgg gagatgcagc caccacatcc cttcatatca   2820
```

```
tactgttttg aataaatttt caaatcctta ttgttcagag ttgtttgggg gttctgtttc    2880
agagcataaa acctaaaggt tatagtagaa caaggcacct tcttaaaaga aatcttgctt    2940
cagaccatca gttacagaga atttcctaaa gtaaaattga agcaactaca acttctcctt    3000
agacactttg gaatctaacc acttaaggac cttttttaaag agatagcttc tcttctttct    3060
gaagatcaat ttctcccaag gccaagattg tccttttctc ccatttcttg ctagctattg    3120
caaatgaggg aagaacatta ttcatctctc ctcccctttt ttttctgatt cttttttcag    3180
tcagttttgc tcctgggttc aagtagtatt accacccttt cacaagcaac agactctcac    3240
agggcaaaaa aaaaaaaaaa aaaaaaaa                                       3268

<210> SEQ ID NO 7
<211> LENGTH: 1424
<212> TYPE: DNA
<213> ORGANISM: Homo sapiens

<400> SEQUENCE: 7
gaaggactgg ggaagactgg atgagaaggg tagaagaggg tgggtgtggg atggggaggg      60
gagagtggaa aggccctggg cagaccctgg cagaaggggc acggggcagg gtgtgagttc     120
cccactagca gggccaggtg agctatggtg ctgcacctac tgctcttctt gctgctgacc     180
ccacagggtg ggcacagctg ccaggggctg gagctggccc gggaacttgt tctggccaag     240
gtgagggccc tgttcttgga tgccttgggg ccccccgcgg tgaccaggga aggtggggac     300
cctggagtca ggcggctgcc ccgaagacat gccctggggg gcttcacaca caggggctct     360
gagcccgagg aagaggagga tgtctcccaa gccatccttt tcccagccac agatgccagc     420
tgtgaggaca agtcagctgc cagagggctg gcccaggagg ctgaggaggg cctcttcaga     480
tacatgttcc ggccatccca gcatacacgc agccgccagg tgacttcagc ccagctgtgg     540
ttccacaccg ggctggacag gcagggcaca gcagcctcca atagctctga gcccctgcta     600
ggcctgctgg cactgtcacc gggaggaccc gtggctgtgc ccatgtcttt gggccatgct     660 cccctcact gggccgtgct gcacctggcc acctctgctc tctctctgct gacccacccc     720
gtcctggtgc tgctgctgcg ctgtcccctc tgtacctgct cagcccggcc tgaggccacg     780
cccttcctgg tggcccacac tcggaccaga ccacccagtg gaggggagag agcccgacgc     840
tcaactcccc tgatgtcctg gccttggtct ccctctgctc tgcgcctgct gcagaggcct     900
ccggaggaac cggctgccca tgccaactgc cacagagtag cactgaacat ctccttccag     960
gagctgggct gggaacggtg gatcgtgtac cctcccagtt tcatcttcca ctactgtcat    1020
ggtggttgtg ggctgcacat cccaccaaac ctgtcccttc cagtccctgg ggctccccct    1080
accccagccc agccctactc cttgctgcca ggggcccagc cctgctgtgc tgctctccca    1140
gggaccatga ggcccctaca tgtccgcacc acctcggatg gaggttactc tttcaagtat    1200
gagacagtgc ccaaccttct cacgcagcac tgtgcttgta tctaagggtg gggggtcttc    1260
cttcttaatc ccatggctgg tggccacgcc cccaccatca tcagctggga ggaaaggcag    1320
agttgggaaa tagatggctc ccactcctcc ctcctttcac ttctctgcct atgggctacc    1380 ctcccccaccc cacttctatc tcaataaaga acacagtgca tatg                    1424

<210> SEQ ID NO 8
<211> LENGTH: 1164
<212> TYPE: DNA
<213> ORGANISM: Gallus gallus

<400> SEQUENCE: 8
```

```
atgtaccaga ccttggccat ctcggcctcg cagggccccg cgccctacga cggatctccg    60
ggcggcttca tgcactccgc gcccagctct cccgtctacg tgcccaccac ccgcgtgggc   120
tccgtgctgc ccacgctgcc ctacctgcag ggcggcggcg cggcccagcc cggccacgct   180
ccggccggcc acgtctggtc gcagccggcg gccgagagcc cctcgtacgg cgccgcgggc   240
ggcgcgcacc cctcgggccg cttcccctac tcggccagcc cgcccgtggc caacggcgcc   300
tcgcgggagc agtacggcgg cggcctggcg gcgagggagc agtacggagc gctgccgcgg   360
ccgctcaacg gctcctaccc ggcgcccctac gcctcctacg tggggccgca gctcggcccc   420
gcctggcccg cggcgcccctt cgagaactcc gtgctgcact gcctgcaggg ccgcgccgcg   480
cccatcccg tgcgggctcc gagcgcagag ctgctggaag acctctccga gagccgcgag   540
tgcgtcaact gcggctccat ccagacccccg ctgtggagga gggacggcac cgggaattac   600
ctgtgcaacg cctgcgggct ctacaccaaa atgaacggcc tgagccggcc cctcatcaaa   660
ccccagaaga gagtgccctc gtcgcggcgg ctcggcctgt cctgtgccaa ctgccacacc   720
accaccacca ccctctggcg ccggaacgcc gagggtgagc ccgtctgcaa cgcctgcggc   780
ctctacatga agcttcatgg ggttccccga ccacttgcta tgaaaaaaga aggaattcag   840
acgaggaaac gaaaacctaa gaacatcaat aagtcgaagg catgctctgg taacagcact   900
actgcagttc ctatgactcc aacatctacg tcttctacta actcagatga ctgtagcaaa   960
aacgcctccc caagcacgca gccggcagcc tcggggggcga gctcgtcagt gatgtccggc  1020
ccaggagaga gcaccagtcc cgaaagcagc aaccttaagt attcaggtca agatgggctg  1080
tacacaggag tcagcctgac ctccacggcc gaggtgacgg cgtccgtcag gcaggatcac  1140
tggtgtgccc tggctctggc gtga                                         1164
```

<210> SEQ ID NO 9
<211> LENGTH: 6
<212> TYPE: PRT
<213> ORGANISM: Artificial sequence
<220> FEATURE:
<223> OTHER INFORMATION: Consensus GATA protein DNA binding domain

<400> SEQUENCE: 9

Trp Gly Ala Thr Ala Arg
1               5

<210> SEQ ID NO 10
<211> LENGTH: 23
<212> TYPE: DNA
<213> ORGANISM: Artificial sequence
<220> FEATURE:
<223> OTHER INFORMATION: Amplification primer

<400> SEQUENCE: 10
tgtggcggag aaatgccagt ggg                                           23

<210> SEQ ID NO 11
<211> LENGTH: 22
<212> TYPE: DNA
<213> ORGANISM: Artificial sequence
<220> FEATURE:
<223> OTHER INFORMATION: Amplification primer

<400> SEQUENCE: 11
cctgtgcctc ccagactgga gc                                            22

```
<210> SEQ ID NO 12
<211> LENGTH: 23
<212> TYPE: DNA
<213> ORGANISM: Artificial sequence
<220> FEATURE:
<223> OTHER INFORMATION: Amplification primer

<400> SEQUENCE: 12
tctgcaacgc ctgtggcctc tac                                          23

<210> SEQ ID NO 13
<211> LENGTH: 23
<212> TYPE: DNA
<213> ORGANISM: Artificial sequence
<220> FEATURE:
<223> OTHER INFORMATION: Amplification primer

<400> SEQUENCE: 13
gatgtgtccg gagtggctga agg                                          23

<210> SEQ ID NO 14
<211> LENGTH: 24
<212> TYPE: DNA
<213> ORGANISM: Artificial sequence
<220> FEATURE:
<223> OTHER INFORMATION: Amplification primer

<400> SEQUENCE: 14
cactctggag gaggaatgcc aatg                                         24

<210> SEQ ID NO 15
<211> LENGTH: 23
<212> TYPE: DNA
<213> ORGANISM: Artificial sequence
<220> FEATURE:
<223> OTHER INFORMATION: Amplification primer

<400> SEQUENCE: 15
agtggctgaa gggcgagatg tgg                                          23

<210> SEQ ID NO 16
<211> LENGTH: 21
<212> TYPE: DNA
<213> ORGANISM: Artificial sequence
<220> FEATURE:
<223> OTHER INFORMATION: Amplification primer

<400> SEQUENCE: 16
ctggcctgtc atctcactac g                                            21

<210> SEQ ID NO 17
<211> LENGTH: 21
<212> TYPE: DNA
<213> ORGANISM: Artificial sequence
<220> FEATURE:
<223> OTHER INFORMATION: Amplification primer

<400> SEQUENCE: 17
ggtccgtgca ggaatttgag g                                            21

<210> SEQ ID NO 18
<211> LENGTH: 21
<212> TYPE: DNA
<213> ORGANISM: Artificial sequence
<220> FEATURE:
<223> OTHER INFORMATION: Amplification primer
```

```
<400> SEQUENCE: 18
tcgccagcac tgacagctca g                                              21

<210> SEQ ID NO 19
<211> LENGTH: 21
<212> TYPE: DNA
<213> ORGANISM: Artificial sequence
<220> FEATURE:
<223> OTHER INFORMATION: Amplification primer

<400> SEQUENCE: 19
tggtctgttc caggctgttc c                                              21

<210> SEQ ID NO 20
<211> LENGTH: 22
<212> TYPE: DNA
<213> ORGANISM: Artificial sequence
<220> FEATURE:
<223> OTHER INFORMATION: Amplification primer

<400> SEQUENCE: 20
ttctaactca gatgattgca gc                                             22

<210> SEQ ID NO 21
<211> LENGTH: 20
<212> TYPE: DNA
<213> ORGANISM: Artificial sequence
<220> FEATURE:
<223> OTHER INFORMATION: Amplification primer

<400> SEQUENCE: 21
gctgcacaaa agcagacacg                                                20

<210> SEQ ID NO 22
<211> LENGTH: 25
<212> TYPE: DNA
<213> ORGANISM: Artificial sequence
<220> FEATURE:
<223> OTHER INFORMATION: Amplification primer

<400> SEQUENCE: 22
cagttaccaa atctactgac aatgc                                          25

<210> SEQ ID NO 23
<211> LENGTH: 24
<212> TYPE: DNA
<213> ORGANISM: Artificial sequence
<220> FEATURE:
<223> OTHER INFORMATION: Amplification primer

<400> SEQUENCE: 23
caagggcaga aatcagaacg tgtc                                           24

<210> SEQ ID NO 24
<211> LENGTH: 22
<212> TYPE: DNA
<213> ORGANISM: Artificial sequence
<220> FEATURE:
<223> OTHER INFORMATION: Amplification primer

<400> SEQUENCE: 24
gccgcatccg ctgcgctgta gc                                             22

<210> SEQ ID NO 25
<211> LENGTH: 22
```

```
<212> TYPE: DNA
<213> ORGANISM: Artificial sequence
<220> FEATURE:
<223> OTHER INFORMATION: Amplification primer

<400> SEQUENCE: 25
tggtgcggcc tgttggtcgg gc                                              22

<210> SEQ ID NO 26
<211> LENGTH: 21
<212> TYPE: DNA
<213> ORGANISM: Artificial sequence
<220> FEATURE:
<223> OTHER INFORMATION: Amplification primer

<400> SEQUENCE: 26
acctactgct cttcttgctg c                                               21

<210> SEQ ID NO 27
<211> LENGTH: 21
<212> TYPE: DNA
<213> ORGANISM: Artificial sequence
<220> FEATURE:
<223> OTHER INFORMATION: Amplification primer

<400> SEQUENCE: 27
cggaacatgt atctgaagag g                                               21

<210> SEQ ID NO 28
<211> LENGTH: 21
<212> TYPE: DNA
<213> ORGANISM: Artificial sequence
<220> FEATURE:
<223> OTHER INFORMATION: Amplification primer

<400> SEQUENCE: 28
tggtcctggt gtccatgctg g                                               21

<210> SEQ ID NO 29
<211> LENGTH: 23
<212> TYPE: DNA
<213> ORGANISM: Artificial sequence
<220> FEATURE:
<223> OTHER INFORMATION: Amplification primer

<400> SEQUENCE: 29
gtcgatggta ttaggataga agc                                             23

<210> SEQ ID NO 30
<211> LENGTH: 23
<212> TYPE: DNA
<213> ORGANISM: Artificial sequence
<220> FEATURE:
<223> OTHER INFORMATION: Amplification primer

<400> SEQUENCE: 30
gatgctgttt cgactccagt gtc                                             23

<210> SEQ ID NO 31
<211> LENGTH: 22
<212> TYPE: DNA
<213> ORGANISM: Artificial sequence
<220> FEATURE:
<223> OTHER INFORMATION: Amplification primer

<400> SEQUENCE: 31
```

```
gagaagcagc acttccgaga gg                                              22
```

<210> SEQ ID NO 32
<211> LENGTH: 20
<212> TYPE: DNA
<213> ORGANISM: Artificial sequence
<220> FEATURE:
<223> OTHER INFORMATION: Amplification primer

<400> SEQUENCE: 32

```
tggccttgct gtcctccagc                                                 20
```

<210> SEQ ID NO 33
<211> LENGTH: 20
<212> TYPE: DNA
<213> ORGANISM: Artificial sequence
<220> FEATURE:
<223> OTHER INFORMATION: Amplification primer

<400> SEQUENCE: 33

```
cctggagtca aagcagcagc                                                 20
```

<210> SEQ ID NO 34
<211> LENGTH: 21
<212> TYPE: DNA
<213> ORGANISM: Artificial sequence
<220> FEATURE:
<223> OTHER INFORMATION: Amplification primer

<400> SEQUENCE: 34

```
gaccacagtc catgccatca c                                               21
```

<210> SEQ ID NO 35
<211> LENGTH: 21
<212> TYPE: DNA
<213> ORGANISM: Artificial sequence
<220> FEATURE:
<223> OTHER INFORMATION: Amplification primer

<400> SEQUENCE: 35

```
gtccaccacc ctgttgctgt a                                               21
```

<210> SEQ ID NO 36
<211> LENGTH: 29
<212> TYPE: DNA
<213> ORGANISM: Artificial sequence
<220> FEATURE:
<223> OTHER INFORMATION: Amplification primer

<400> SEQUENCE: 36

```
tttgtatagt tttgtagttt gtgtttagt                                       29
```

<210> SEQ ID NO 37
<211> LENGTH: 24
<212> TYPE: DNA
<213> ORGANISM: Artificial sequence
<220> FEATURE:
<223> OTHER INFORMATION: Amplification primer

<400> SEQUENCE: 37

```
cccaactcac aactcaaatc ccca                                            24
```

<210> SEQ ID NO 38
<211> LENGTH: 26
<212> TYPE: DNA
<213> ORGANISM: Artificial sequence

```
<220> FEATURE:
<223> OTHER INFORMATION: Amplification primer

<400> SEQUENCE: 38
gtatagtttc gtagtttgcg tttagc                                              26

<210> SEQ ID NO 39
<211> LENGTH: 21
<212> TYPE: DNA
<213> ORGANISM: Artificial sequence
<220> FEATURE:
<223> OTHER INFORMATION: Amplification primer

<400> SEQUENCE: 39
aactcgcgac tcgaatcccc g                                                   21

<210> SEQ ID NO 40
<211> LENGTH: 29
<212> TYPE: DNA
<213> ORGANISM: Artificial sequence
<220> FEATURE:
<223> OTHER INFORMATION: Amplification primer

<400> SEQUENCE: 40
tggagtttgt ttttaggtta gttttttggt                                          29

<210> SEQ ID NO 41
<211> LENGTH: 29
<212> TYPE: DNA
<213> ORGANISM: Artificial sequence
<220> FEATURE:
<223> OTHER INFORMATION: Amplification primer

<400> SEQUENCE: 41
caaaccaata caactaaaca aacaaacca                                           29

<210> SEQ ID NO 42
<211> LENGTH: 26
<212> TYPE: DNA
<213> ORGANISM: Artificial sequence
<220> FEATURE:
<223> OTHER INFORMATION: Amplification primer

<400> SEQUENCE: 42
agttcgtttt taggttagtt ttcggc                                              26

<210> SEQ ID NO 43
<211> LENGTH: 25
<212> TYPE: DNA
<213> ORGANISM: Artificial sequence
<220> FEATURE:
<223> OTHER INFORMATION: Amplification primer

<400> SEQUENCE: 43
ccaatacaac taaacgaacg aaccg                                               25

<210> SEQ ID NO 44
<211> LENGTH: 24
<212> TYPE: DNA
<213> ORGANISM: Artificial sequence
<220> FEATURE:
<223> OTHER INFORMATION: Amplification primer

<400> SEQUENCE: 44
gtgtggggta gattttggat ttgt                                                24
```

<210> SEQ ID NO 45
<211> LENGTH: 24
<212> TYPE: DNA
<213> ORGANISM: Artificial sequence
<220> FEATURE:
<223> OTHER INFORMATION: Amplification primer

<400> SEQUENCE: 45
aaacaaccaa acctcaaaca aaca                                      24

<210> SEQ ID NO 46
<211> LENGTH: 21
<212> TYPE: DNA
<213> ORGANISM: Artificial sequence
<220> FEATURE:
<223> OTHER INFORMATION: Amplification primer

<400> SEQUENCE: 46
cggggtagat ttcggattcg c                                         21

<210> SEQ ID NO 47
<211> LENGTH: 21
<212> TYPE: DNA
<213> ORGANISM: Artificial sequence
<220> FEATURE:
<223> OTHER INFORMATION: Amplification primer

<400> SEQUENCE: 47
caaccgaacc tcgaacgaac g                                         21

<210> SEQ ID NO 48
<211> LENGTH: 29
<212> TYPE: DNA
<213> ORGANISM: Artificial sequence
<220> FEATURE:
<223> OTHER INFORMATION: Amplification primer

<400> SEQUENCE: 48
gaattatatt ttttgttggg agtggttgt                                 29

<210> SEQ ID NO 49
<211> LENGTH: 27
<212> TYPE: DNA
<213> ORGANISM: Artificial sequence
<220> FEATURE:
<223> OTHER INFORMATION: Amplification primer

<400> SEQUENCE: 49
ccaactaact attacctcca taaaaca                                   27

<210> SEQ ID NO 50
<211> LENGTH: 23
<212> TYPE: DNA
<213> ORGANISM: Artificial sequence
<220> FEATURE:
<223> OTHER INFORMATION: Amplification primer

<400> SEQUENCE: 50
tatttttcgt cgggagtggt cgc                                       23

<210> SEQ ID NO 51
<211> LENGTH: 25
<212> TYPE: DNA
<213> ORGANISM: Artificial sequence
<220> FEATURE:
<223> OTHER INFORMATION: Amplification primer

<400> SEQUENCE: 51
gactaactat tacctccgta aaacg  25

<210> SEQ ID NO 52
<211> LENGTH: 27
<212> TYPE: DNA
<213> ORGANISM: Artificial sequence
<220> FEATURE:
<223> OTHER INFORMATION: Amplification primer

<400> SEQUENCE: 52
ggtggttagt agtaggttgt gttttgt  27

<210> SEQ ID NO 53
<211> LENGTH: 31
<212> TYPE: DNA
<213> ORGANISM: Artificial sequence
<220> FEATURE:
<223> OTHER INFORMATION: Amplification primer

<400> SEQUENCE: 53
cctatacaaa taataaataa caccaaaacc a  31

<210> SEQ ID NO 54
<211> LENGTH: 24
<212> TYPE: DNA
<213> ORGANISM: Artificial sequence
<220> FEATURE:
<223> OTHER INFORMATION: Amplification primer

<400> SEQUENCE: 54
ggttagtagt aggtcgtgtt tcgc  24

<210> SEQ ID NO 55
<211> LENGTH: 26
<212> TYPE: DNA
<213> ORGANISM: Artificial sequence
<220> FEATURE:
<223> OTHER INFORMATION: Amplification primer

<400> SEQUENCE: 55
acgaataata aataacgccg aaaccg  26

<210> SEQ ID NO 56
<211> LENGTH: 30
<212> TYPE: DNA
<213> ORGANISM: Artificial sequence
<220> FEATURE:
<223> OTHER INFORMATION: Amplification primer

<400> SEQUENCE: 56
tagtggagat tattgtttta gaggattttt  30

<210> SEQ ID NO 57
<211> LENGTH: 28
<212> TYPE: DNA
<213> ORGANISM: Artificial sequence
<220> FEATURE:
<223> OTHER INFORMATION: Amplification primer

<400> SEQUENCE: 57
tcaaaaataa aaaccaccc aaaccca  28

<210> SEQ ID NO 58

```
<211> LENGTH: 28
<212> TYPE: DNA
<213> ORGANISM: Artificial sequence
<220> FEATURE:
<223> OTHER INFORMATION: Amplification primer

<400> SEQUENCE: 58
gtggagatta ttgttttaga ggattttc                                    28

<210> SEQ ID NO 59
<211> LENGTH: 25
<212> TYPE: DNA
<213> ORGANISM: Artificial sequence
<220> FEATURE:
<223> OTHER INFORMATION: Amplification primer

<400> SEQUENCE: 59
aaaataaaaa accgcccgaa ccccg                                       25

<210> SEQ ID NO 60
<211> LENGTH: 27
<212> TYPE: DNA
<213> ORGANISM: Artificial sequence
<220> FEATURE:
<223> OTHER INFORMATION: Amplification primer

<400> SEQUENCE: 60
taataaagtt gattttgggt attatag                                     27

<210> SEQ ID NO 61
<211> LENGTH: 25
<212> TYPE: DNA
<213> ORGANISM: Artificial sequence
<220> FEATURE:
<223> OTHER INFORMATION: Amplification primer

<400> SEQUENCE: 61
ccctacctac taaacctaaa aattc                                       25

<210> SEQ ID NO 62
<211> LENGTH: 31
<212> TYPE: DNA
<213> ORGANISM: Artificial sequence
<220> FEATURE:
<223> OTHER INFORMATION: Amplification primer

<400> SEQUENCE: 62
gttttagtta gtgtatttag ttttagttta g                                31

<210> SEQ ID NO 63
<211> LENGTH: 26
<212> TYPE: DNA
<213> ORGANISM: Artificial sequence
<220> FEATURE:
<223> OTHER INFORMATION: Amplification primer

<400> SEQUENCE: 63
ccacttaacc ctaacaaacc ctactc                                      26

<210> SEQ ID NO 64
<211> LENGTH: 22
<212> TYPE: DNA
<213> ORGANISM: Artificial sequence
<220> FEATURE:
<223> OTHER INFORMATION: Amplification primer

<400> SEQUENCE: 64
```
gtgagtttaa ttaggagttt ag                                           22

<210> SEQ ID NO 65
<211> LENGTH: 22
<212> TYPE: DNA
<213> ORGANISM: Artificial sequence
<220> FEATURE:
<223> OTHER INFORMATION: Amplification primer

<400> SEQUENCE: 65
atatccctaa aacctaaaaa cc                                           22

<210> SEQ ID NO 66
<211> LENGTH: 28
<212> TYPE: DNA
<213> ORGANISM: Artificial sequence
<220> FEATURE:
<223> OTHER INFORMATION: Amplification primer

<400> SEQUENCE: 66
tattgtaaaa gaattagttt aggtttag                                     28

<210> SEQ ID NO 67
<211> LENGTH: 24
<212> TYPE: DNA
<213> ORGANISM: Artificial sequence
<220> FEATURE:
<223> OTHER INFORMATION: Amplification primer

<400> SEQUENCE: 67
taaccattac ctcctctcta ctcc                                         24

<210> SEQ ID NO 68
<211> LENGTH: 31
<212> TYPE: DNA
<213> ORGANISM: Artificial sequence
<220> FEATURE:
<223> OTHER INFORMATION: Amplification primer

<400> SEQUENCE: 68
gtgattttgt gtgtgtttag ttttagattt g                                 31

<210> SEQ ID NO 69
<211> LENGTH: 26
<212> TYPE: DNA
<213> ORGANISM: Artificial sequence
<220> FEATURE:
<223> OTHER INFORMATION: Amplification primer

<400> SEQUENCE: 69
ccctccaaaa cacataaccc caaaac                                       26

<210> SEQ ID NO 70
<211> LENGTH: 30
<212> TYPE: DNA
<213> ORGANISM: Artificial sequence
<220> FEATURE:
<223> OTHER INFORMATION: Amplification primer

<400> SEQUENCE: 70
gtagggtttt gatttattta gagttgtttg                                   30

<210> SEQ ID NO 71
<211> LENGTH: 28
<212> TYPE: DNA

-continued

```
<213> ORGANISM: Artificial sequence
<220> FEATURE:
<223> OTHER INFORMATION: Amplification primer

<400> SEQUENCE: 71
aaccaaaacc aaccccaaca tacaaaac                                        28
```